United States Patent
Xu et al.

(10) Patent No.: US 10,155,775 B2
(45) Date of Patent: Dec. 18, 2018

(54) SUBSTITUTED AMINO SIX-MEMBERED SATURATED HETEROALICYCLES AS LONG-ACTING DPP-IV INHIBITORS

(71) Applicants: Centaurus Biopharma Co., Ltd., Beijing (CN); Chia Tai Tianqing Pharmaceutical Group Co., Ltd., Haizhou District (CN); Lianyungang Runzhong Pharmaceutical Co., Ltd., Lianyungang, Jiangsu (CN)

(72) Inventors: Xinhe Xu, Beijing (CN); Yu Shen, Beijing (CN); Dengming Xiao, Beijing (CN); Hong Luo, Beijing (CN); Yong Peng, Beijing (CN); Yongxin Han, Beijing (CN); Aiming Zhang, Lianyungang (CN); Ling Yang, Lianyungang (CN)

(73) Assignees: Centaurus Biopharma Co., Ltd., Beijing (CN); Chia Tai Tianqing Pharmaceutical Co., Ltd., Lianyungang, Jiangsu (CN); Lianyungang Runzhong Pharmaceutical Co., Ltd., Lianyungang, Jiangsu (CN)

(*) Notice: Subject to any disclaimer, the term of this patent is extended or adjusted under 35 U.S.C. 154(b) by 0 days.

(21) Appl. No.: 15/549,773

(22) PCT Filed: Feb. 4, 2016

(86) PCT No.: PCT/CN2016/073539
§ 371 (c)(1),
(2) Date: Aug. 9, 2017

(87) PCT Pub. No.: WO2016/127916
PCT Pub. Date: Aug. 18, 2016

(65) Prior Publication Data
US 2018/0111950 A1    Apr. 26, 2018

(30) Foreign Application Priority Data
Feb. 12, 2015 (CN) .......................... 2015 1 0076191

(51) Int. Cl.
| | | |
|---|---|---|
| C07D 513/04 | (2006.01) |
| C07D 487/04 | (2006.01) |
| C07D 495/04 | (2006.01) |
| C07D 405/04 | (2006.01) |
| A61K 31/542 | (2006.01) |
| A61K 31/4162 | (2006.01) |
| A61K 31/407 | (2006.01) |
| A61K 31/4035 | (2006.01) |
| A61P 3/10 | (2006.01) |
| A61P 5/50 | (2006.01) |
| C07D 513/14 | (2006.01) |
| A61P 7/00 | (2006.01) |
| A61P 3/04 | (2006.01) |
| A61P 1/00 | (2006.01) |
| A61P 25/00 | (2006.01) |

(52) U.S. Cl.
CPC .......... *C07D 513/14* (2013.01); *A61K 31/407* (2013.01); *A61K 31/4035* (2013.01); *A61K 31/4162* (2013.01); *A61K 31/542* (2013.01); *A61P 1/00* (2018.01); *A61P 3/04* (2018.01); *A61P 7/00* (2018.01); *A61P 25/00* (2018.01); *C07D 405/04* (2013.01); *C07D 487/04* (2013.01); *C07D 495/04* (2013.01)

(58) Field of Classification Search
CPC .. C07D 513/04; C07D 487/04; C07D 495/04; C07D 405/04; A61K 31/5542; A61K 31/4162; A61K 31/407; A61K 31/4035
USPC ...... 548/428, 452, 453; 546/268.1; 514/337, 514/338, 340, 411, 412
See application file for complete search history.

(56) References Cited

FOREIGN PATENT DOCUMENTS

| WO | 2007/087231 A2 | 8/2007 |
| WO | 2007/097931 A2 | 8/2007 |
| WO | 2007/126745 A2 | 11/2007 |
| WO | 2008/060488 A1 | 5/2008 |

(Continued)

OTHER PUBLICATIONS

Kwok et al. Trends in Cardiovascular MeDicine 24 (2014)157-164.*

(Continued)

*Primary Examiner* — Venkataraman Balasubramanian
(74) *Attorney, Agent, or Firm* — Kilpatrick Townsend & Stockton LLP

(57) ABSTRACT

The present application relates to a substituted amino six-membered saturated heteroalicycle represented by formula I as a long-acting DPP-IV inhibitor, a method for preparing the same, a pharmaceutical composition comprising the same, and a use of the same in treating and/or preventing diseases and disorders benefitting from DPP-IV inhibition.

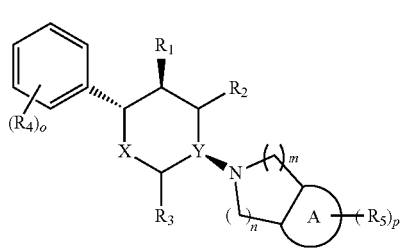

19 Claims, 1 Drawing Sheet

(56) References Cited

FOREIGN PATENT DOCUMENTS

WO 2010/056708 A1 5/2010
WO 2011103256 A1 8/2011

OTHER PUBLICATIONS

Vijayakumar et al. Current Therapeutic Research 84 (2017) 4-9.*
Cecil Textbook of Medicine, edited by Bennet, J.C., and Plum F., 20th edition, vol. 1, 1004-1010, 1996.*
Dermer et al., Bio/Technology, 1994, 12:320.*
Freshney et al., Culture of Animal Cells, A Manual of Basic Technique, Alan R. Liss, Inc., 1983, New York, p. 4.*
Golub et al., Science, 286, 531-537, 1999.*
Vippagunta et al., Advanced Drug Delivery Reviews 48: 3-26, 2001.*
Ulrich, Crystallization, Kirk-Othmer Encyclopedia of Chemical Technology, pp. 1-7, 2002.*
International Search Report dated May 10, 2016 in PCT/CN2016/073539, 5 pages.
Extended European Search Report in EP16748717.2, dated Jun. 28, 2018, 9 pages.

* cited by examiner

SUBSTITUTED AMINO SIX-MEMBERED SATURATED HETEROALICYCLES AS LONG-ACTING DPP-IV INHIBITORS

CROSS REFERENCE TO RELATED APPLICATIONS

This application is a U.S. National Phase Application of PCT/CN2016/073539, International Filing Date Feb. 4, 2016, which claims priority to Chinese Application No. 20151007619.4, filing date Feb. 12, 2015, the disclosures of which are incorporated herein by reference for all purposes.

TECHNICAL FIELD

The present application relates to a novel amino six-membered saturated heteroalicyclic derivative with dipeptidyl peptidase-IV (DPP-IV) long-acting inhibitory activity, a preparation process thereof, a pharmaceutical composition thereof, and a use in the treatment of diseases and disorders benefitting from DPP-IV inhibition.

BACKGROUND

Dipeptidyl peptidase-IV (DPP-IV) is a serine protease that can rapidly cleave a protein in which an amino acid at the N-terminus of a peptide chain is proline or alanine, is responsible for a metabolic cleavage of some endogenous peptides (such as GLP-1 and GIP) in vivo, and has shown to have a proteolytic activity against a variety of other peptides such as GHRH, NPY, GLP-2 and VIP in vitro. Because of the degradation of DPP-IV, GLP-1 and GIP are rapidly inactivated in vivo, thus inhibiting the activity of DPP-IV would greatly prolong physiological activity duration of GLP-1 and GIP in vivo, which indirectly regulate the insulin secretion and ultimately play a role in controlling a blood glucose level.

As a novel means for treating diabetes, DPP-IV inhibitors can glucose-dependently stimulate insulin secretion, is not prone to have hypoglycemic side effects upon controlling a blood glucose level, and also have some advantages, such as preserving islet β cell function, having few gastrointestinal tract side effects, good tolerance, and the like. DPP-IV inhibitors can be administered orally without the need for injection, and is comparable to existing oral hypoglycemic agents in therapeutic efficacy.

Based on the above features, DPP-IV inhibitors are useful in the treatment and/or prophylaxis of DPP-IV mediated diseases and disorders, such as diabetes, obesity, and the like, particularly type II diabetes.

Currently, eight DPP-IV inhibitors have successfully marketed, which are sitagliptin, vildagliptin, saxagliptin, linagliptin, alogliptin, anagliptin, gemigliptin, and teneligliptin; five DPP-IV inhibitors are in the Phase II/III clinical study; and more DPP-IV inhibitors are in Phase I clinical study and pre-clinical study phase.

Because diabetes is a chronic disease, and patients need lifelong medication, the convenience of medication has a direct impact on whether patients could adhere to treatment. Accordingly, there is an urgent need for novel DPP-IV inhibitors, particularly for long-acting DPP-IV inhibitors.

SUMMARY OF THE INVENTION

In one aspect, the present application provides a compound of formula I or a pharmaceutically acceptable salt thereof:

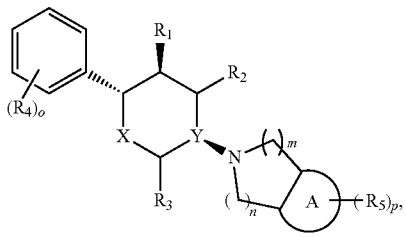

wherein
Ring A is selected from the group consisting of 6-membered aryl and 5-6 membered heteroaryl containing 1 to 2 heteroatoms selected from the group consisting of N, O and S atoms;
X is selected from the group consisting of O and $CH_2$;
Y is selected from the group consisting of N and CH; and when X is $CH_2$, Y is not CH;
$R_1$, $R_2$ and $R_3$ are each independently selected from the group consisting of H, $C_{1-3}$ alkyl, $-NH_2$ and $-OH$;
each $R_4$ is independently selected from the group consisting of halogen, $-NH_2$, $-OH$, $C_{1-6}$ alkyl, $C_{1-6}$ alkoxy, phenoxy and benzyloxy;
each $R_5$ is independently selected from the group consisting of $C_{1-6}$ alkyl, halogen, $-CN$, $-OH$, $-COOR_6$, $-NHR_7$ and $-SO_2R_8$, or two $R_5$ groups together with the atoms of Ring A to which they are attached form a 5-7 membered ring;
$R_6$ is selected from the group consisting of H and $C_{1-6}$ alkyl;
$R_7$ is selected from the group consisting of H, $C_{1-6}$ alkyl and $-SO_2R_8$;
each $R_8$ is independently selected from the group consisting of $-OH$, $-NH_2$, $C_{1-6}$ alkyl and $C_{3-6}$ cycloalkyl;
o and p are each independently 1, 2 or 3; and
m and n are each independently 1 or 2.

In another aspect, the present application provides a pharmaceutical composition comprising a compound of formula I or a pharmaceutically acceptable salt, solvate, polymorph, metabolite thereof as an active ingredient, and one or more pharmaceutically acceptable carriers.

In yet another aspect, the present application provides a use of a compound of formula I or a pharmaceutically acceptable salt, solvate, polymorph, metabolite thereof or a pharmaceutical composition thereof in the preparation of a medicament for the treatment of diseases and disorders benefitting from DPP-IV inhibition.

In yet another aspect, the present application provides a method for treating diseases and disorders benefitting from DPP-IV inhibition, comprising administering to a subject in need thereof a compound of formula I or a pharmaceutically acceptable salt, solvate, polymorph, metabolite thereof or a pharmaceutical composition thereof.

In yet another aspect, the present application provides a compound of formula I or a pharmaceutically acceptable salt, solvate, polymorph, metabolite thereof or a pharmaceutical composition thereof for use in a method for the treatment of diseases and disorders benefitting from DPP-IV inhibition.

DETAILED DESCRIPTION OF THE INVENTION

Figure 1:
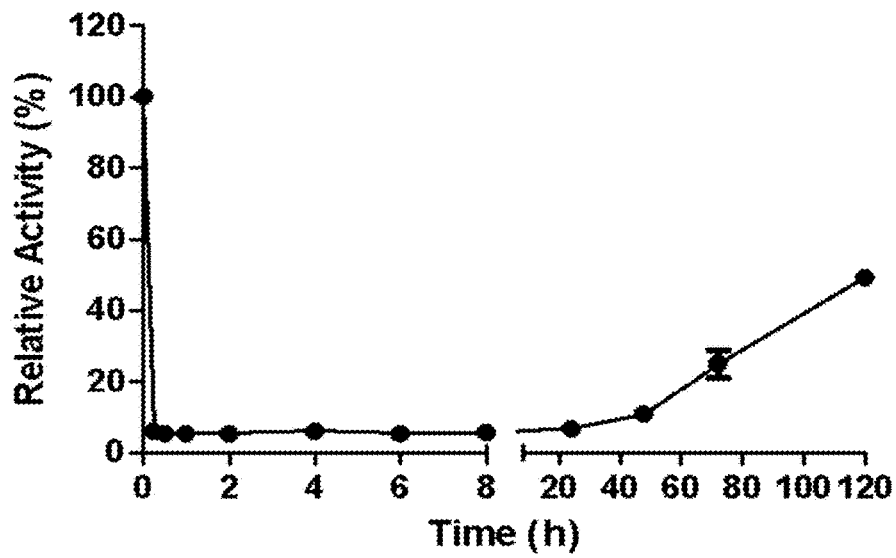
FIG. 1 shows in vitro experimental results of a compound of Example 4 in inhibiting plasma DPP-IV activity in rats. When an oral dose was 5 mg/kg body weight, the compound of Example 4 inhibited the plasma DPP-IV activity in rats by almost 50% at 120 hour, meeting the requirement of long-acting inhibitors.
Figure 2:
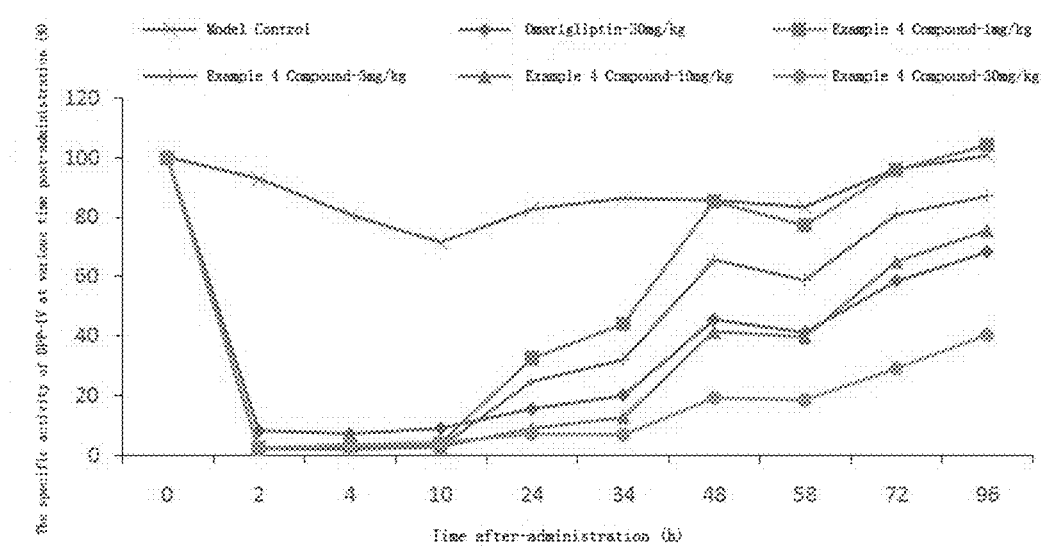
FIG. 2 shows experimental results of the compound of Example 4 and Omarigliptin in inhibiting serum DPP-IV activity in ob/ob mice after a single administration at various doses.

In the following description, certain specific details are included to provide a thorough understanding of various disclosed embodiments. However, those skilled in the relevant art will recognize that the embodiments may be practiced without one or more of these specific details, or with other methods, components, materials, and the like.

Unless the context requires otherwise, throughout the specification and claims which follow, the term "comprise" and English variations thereof, such as "comprises" and "comprising", are to be construed in an open and inclusive sense, that is as, "including, but not limited to".

Reference throughout this specification to "one embodiment", or "an embodiment", or "another embodiment", or "some embodiments" means that a particular referent element, structure, or characteristics described in connection with the embodiment is included in at least one embodiment. Accordingly, the appearances of the phase "in one embodiment", or "in an embodiment", or "in another embodiment", or "in some embodiments" in various places throughout this specification are not necessarily all referring to the same embodiment. In addition, the particular elements, structures, or characteristics may be combined in any suitable manner in one or more embodiments.

It should be noted that, as used in this specification and the appended claims, the singular forms "a", "an" and "the" include plural referents unless the content clearly dictates otherwise. Thus, for example, reference to a reaction in which "a catalyst" is involved includes a single catalyst, or two or more catalysts. Unless otherwise explicitly specified herein, it should also be noted that the term "or" is generally employed in its sense including "and/or" unless the content clearly dictates otherwise.

Chemical Terms and Definitions

As used herein, the term "compound" comprises all stereoisomers, geometric isomers, tautomers and isotopic forms thereof.

Compounds of the present application may be asymmetric, for example, having one or more stereoisomers. Unless otherwise indicated, all stereoisomers, such as enantiomers and diastereomers, are included within the scope of the present application. Compounds containing asymmetric carbon atom(s) of the present application can be isolated in an optically active pure form or a racemic form. The optically active pure form can be isolated through the resolution of a racemic mixture, or synthesized from chiral raw material(s) or chiral reagent(s).

Compounds of the present application also include tautomeric forms. Tautomeric forms are derived from the switching of a single bond and an adjacent double bond associated with the migration of a proton.

All isotopic atoms are also included in the present application, either in an intermediate or in a final compound. The isotopic atoms have the same atomic number but different mass number. For example, isotopic hydrogen includes tritium and deuterium.

The term "halogen" refers to F, Cl, Br or I.
The term "hydroxy" refers to —OH.
The term "carboxy" refers to —COOH.
The term "cyano" refers to —CN.
As used herein, the term "sulfonyl" refers to —$SO_2$-alkyl, —$SO_2$-cycloalkyl and —$SO_2$-aryl.

As used herein, the term "amino" refers to —$NH_2$, —NH(alkyl) and —N(alkyl)$_2$. Specific examples of amino include, but are not limited to —$NH_2$, —$NHCH_3$, —NHCH$(CH_3)_2$, —N$(CH_3)_2$, —$NHC_2H_5$, —N$(CH_3)C_2H_5$, and the like.

As used herein, the term "alkyl" refers to a linear or branched saturated aliphatic hydrocarbyl group consisting of carbon atom(s) and hydrogen atoms, such as methyl, ethyl, propyl, butyl, pentyl, hexyl, heptyl, octyl, nonyl, decyl, and the like. The particular alkyl includes all isomers thereof. For example, propyl includes —$CH_2CH_2CH_3$ and —CH$(CH_3)_2$; and butyl includes —$CH_2CH_2CH_2CH_3$, —CH$(CH_3)(CH_2CH_3)$, —C$(CH_3)_3$ and —$CH_2CH(CH_3)_2$. The term "$C_{1-6}$ alkyl" refers to alkyl having 1 to 6 carbon atom(s). The term "$C_{1-4}$ alkyl" refers to alkyl having 1 to 4 carbon atom(s). The term "$C_{1-3}$ alkyl" refers to alkyl having 1 to 3 carbon atom(s). The term "alkyl", "$C_{1-8}$ alkyl", "$C_{1-6}$ alkyl" or "$C_{1-3}$ alkyl" may be unsubstituted or substituted by one or more substituents independently selected from the group consisting of hydroxy, halogen and amino.

As used herein, the term "cycloalkyl" refers to a cyclic saturated hydrocarbyl group consisting of carbon atoms and hydrogen atoms, such as $C_{3-20}$ cycloalkyl, preferably $C_{3-6}$ cycloalkyl, such as cyclopropyl, cyclobutyl, cyclopentyl, cyclohexyl, and the like. The cycloalkyl may be unsubstituted or substituted independently by one or more substituents, including, but not limited to, alkyl, alkoxy, cyano, carboxy, aryl, heteroaryl, amino, halogen, sulfonyl, sulfinyl, phosphoryl and hydroxy.

As used herein, the term "aryl" refers to an all-carbon monocyclic or fused ring which has a completely conjugated π-electron system with 6-14 carbon atoms, preferably 6-12 carbon atoms, most preferably 6 carbon atoms. The aryl may be unsubstituted or substituted independently by one or more substituents, including, but not limited to, alkyl, alkoxy, aryl, arylalkyl, amino, halogen, hydroxy, sulfonyl, sulfinyl, phosphoryl and heteroalicyclyl. Non-limiting examples of aryl include, but are not limited to, phenyl, naphthyl and anthracenyl.

As used herein, the term "arylalkyl" refers to alkyl substituted by aryl as defined above, preferably $C_{1-6}$ alkyl substituted by aryl. Non-limiting examples of arylalkyl include, but are not limited to, —$CH_2$-phenyl, —$(CH_2)_2$-phenyl, —$(CH_2)_3$-phenyl, —CH$(CH_3)$-phenyl, —$CH_2$—CH$(CH_3)$-phenyl, —$(CH_2)_4$-phenyl, —$CH_2$—CH$(CH_3)$—$CH_2$-phenyl, —$CH_2$—$CH_2$—CH$(CH_3)$-phenyl, and the like.

As used herein, the term "heteroaryl" refers to a 5-12 membered monocyclic or fused ring having a completely conjugated π-electron system with 5, 6, 7, 8, 9, 10, 11 or 12 ring atoms, among which 1, 2, 3 or 4 ring atom(s) is(are) independently selected from the group consisting of N, O, and S, and the rest of ring atom(s) is(are) C. The heteroaryl may be unsubstituted or substituted independently by one or more substituents including, but not limited to, alkyl, alkoxy, aryl, arylalkyl, amino, halogen, hydroxy, cyano, nitro, carbonyl and heteroalicyclyl. Non-limiting examples of heteroaryl groups include, but are not limited to, pyrrolyl, furyl, thienyl, imidazolyl, oxazolyl, pyrazolyl, pyridinyl, pyrimidinyl, pyrazinyl, quinolyl, isoquinolyl, tetrazolyl, and triazinyl.

As used herein, the term "heteroarylalkyl" refers to alkyl substituted by heteroaryl as defined above, preferably C$_{1-6}$ alkyl substituted by heteroaryl. Non-limiting examples of heteroarylalkyl include, but are not limited to, —CH$_2$-pyrazolyl, —(CH$_2$)$_2$-pyridinyl, —(CH$_2$)$_3$-thienyl, —CH(CH$_3$)-pyrazinyl, —CH$_2$—CH(CH$_3$)-furyl, and the like.

As used herein, the term "heteroalicycle" refers to a 3-12 membered monocyclic or fused ring having 3, 4, 5, 6, 7, 8, 9, 10, 11 or 12 ring atoms, among which 1 or 2 ring atom(s) is(are) heteroatom(s) independently selected from the group consisting of N, O, and (S)$_n$ (wherein n is 0, 1 or 2) and the rest of ring atom(s) is(are) C. Such a ring may be saturated or unsaturated (e.g., having one or more double bonds), but it does not have a completely conjugated π-electron system. Examples of 3-membered saturated heteroalicycle include, but are not limited to,

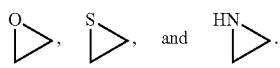

Examples of 4-membered saturated heteroalicycle include, but are not limited to,

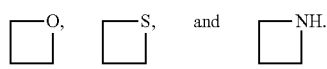

Examples of 5-membered saturated heteroalicycle include, but are not limited to,

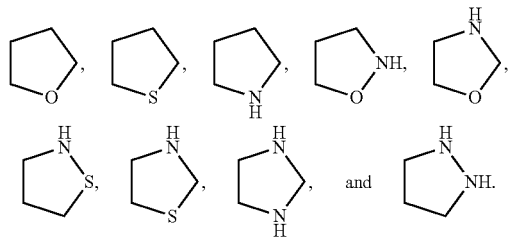

Examples of 6-membered saturated heteroalicycle include, but are not limited to,

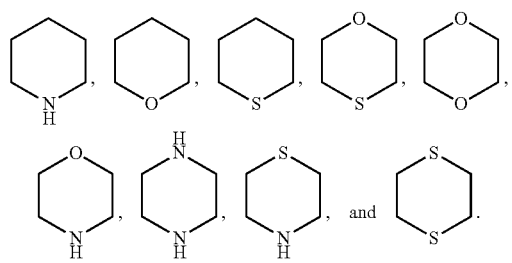

Examples of 7-membered saturated heteroalicycle include, but are not limited to,

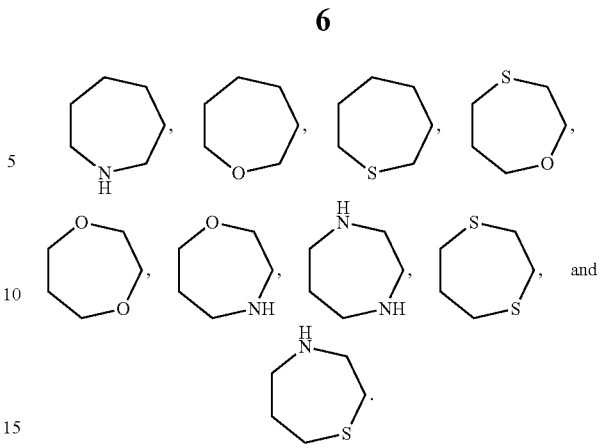

Examples of 5-membered unsaturated heteroalicycle include, but are not limited to,

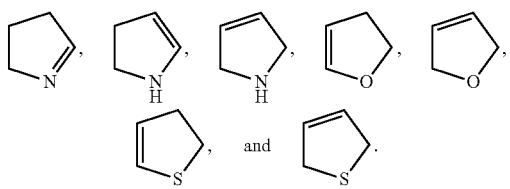

Examples of 6-membered unsaturated heteroalicycle include, but are not limited to,

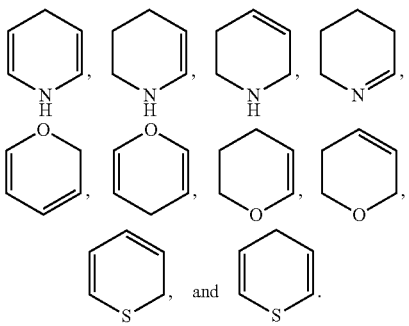

As used herein, the term "heteroalicyclyl" refers to the remaining group after one hydrogen atom is removed from a "heteroalicycle" molecule. Heteroalicyclyl may be unsubstituted or each hydrogen atom of the heteroalicyclyl may be substituted independently by one or more substituents including, but not limited to, alkyl, alkoxy, =O, aryl, arylalkyl, —COOH, —CN, amino, halogen or hydroxy.

As used herein, the term "pharmaceutically acceptable salt" refers to a salt which retains the biological effectiveness and properties of the DPP-IV inhibitors of the present application and is not biologically or otherwise undesirable. For example, a pharmaceutically acceptable salt does not interfere with a beneficial effect of the agents of the present application in inhibiting DPP-IV, including "a pharmaceutically acceptable acid addition salt" and "a pharmaceutically acceptable base addition salt".

As used herein, the term "pharmaceutically acceptable acid addition salt" refers to those salts which retain the biological effectiveness and properties of the free base, are biologically or otherwise desirable, and are formed with inorganic or organic acids.

As used herein, the term "pharmaceutically acceptable base addition salt" refers to those salts which retain the biological effectiveness and properties of the free acid, and are biologically or otherwise desirable. These salts are prepared from addition of an inorganic base or an organic base to the free acid.

As used herein, the term "pharmaceutical composition" refers to a formulation which comprises one or more compounds of the present application or salts thereof and a carrier that is generally accepted in the art for the delivery of a biologically active compound to an organism (e.g., human). The purpose of pharmaceutical composition is to facilitate the administration of the compounds of the present application to the organism.

As used herein, the term "pharmaceutical acceptable carrier" refers to those carriers which do not cause significant stimulation to an organism (e.g., human), and will not impair the bioactivity and properties of an active compound. The "pharmaceutical acceptable carrier" also refers to an inert substance which is administered together with an active ingredient and is beneficial to the administration thereof, including, but not limited to, any glidants, sweetening agents, diluents, preservatives, dyes/colorants, flavoring agents, surfactants, wetting agents, dispersants, disintegrants, suspending agents, stabilizers, isotonic agents, solvents and emulsifiers, which have been approved by the United States Food and Drug Administration as being acceptable for use in humans or animals (such as livestock). Non-limiting examples of a carrier include calcium carbonate, calcium phosphate, various sugars and starches, cellulose derivatives, gelatine, vegetable oils and polyethylene glycols.

Compound of Formula I

In one aspect, the present application provides a compound of formula I or a pharmaceutically acceptable salt thereof:

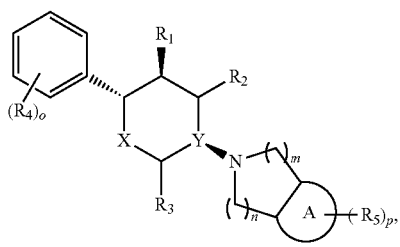

I wherein

Ring A is selected from the group consisting of 6-membered aryl and 5-6 membered heteroaryl containing 1 to 2 heteroatoms selected from the group consisting of N, O and S atoms;

X is selected from the group consisting of O and $CH_2$;
Y is selected from the group consisting of N and CH; and when X is $CH_2$, Y is not CH;

$R_1$, $R_2$ and $R_3$ are each independently selected from the group consisting of H, $C_{1-3}$ alkyl, —$NH_2$ and —OH;

each $R_4$ is independently selected from the group consisting of halogen, —$NH_2$, —OH, $C_{1-6}$ alkyl, $C_{1-6}$ alkoxy, phenoxy and benzyloxy;

each $R_5$ is independently selected from the group consisting of $C_{1-6}$ alkyl, halogen, —CN, —OH, —$COOR_6$, —$NHR_7$ and —$SO_2R_8$, or two $R_5$ groups together with the atoms of Ring A to which they are attached form a 5-7 membered ring;

$R_6$ is selected from the group consisting of H and $C_{1-6}$ alkyl;

$R_7$ is selected from the group consisting of H, $C_{1-6}$ alkyl and —$SO_2R_8$;

each $R_8$ is independently selected from the group consisting of —OH, —$NH_2$, $C_{1-6}$ alkyl and $C_{3-6}$ cycloalkyl;

o and p are each independently 1, 2 or 3; and
m and n are each independently 1 or 2.

In another aspect, the present application provides a compound of formula II or a pharmaceutically acceptable salt thereof:

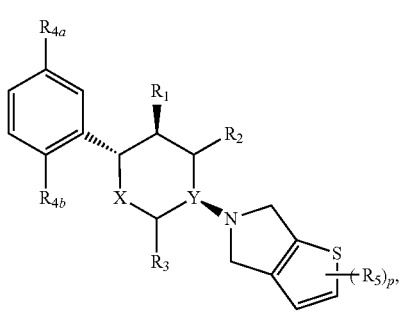

II wherein,
X is O;
Y is selected from the group consisting of N and CH;
$R_1$ is selected from the group consisting of —$NH_2$ and —OH;
$R_2$ and $R_3$ are both H;
$R_{4a}$ and $R_{4b}$ are each independently selected from the group consisting of F, Cl, Br, I, —$NH_2$ and —OH;
each $R_5$ is independently selected from the group consisting of F, Cl, Br, I, —CN, —$COOR_6$, —$NHR_7$ and —$SO_2R_8$;
p is 1 or 2;
$R_6$ is selected from the group consisting of H, methyl, ethyl, propyl and butyl;
$R_7$ is selected from the group consisting of H, methyl, ethyl, propyl, butyl and —$SO_2R_8$; each $R_8$ is independently selected from the group consisting of —OH, —$NH_2$, methyl, ethyl, propyl, butyl, $C_3$ cycloalkyl, $C_4$ cycloalkyl and $C_5$ cycloalkyl.

In another aspect, the present application provides a compound of formula III or a pharmaceutically acceptable salt thereof:

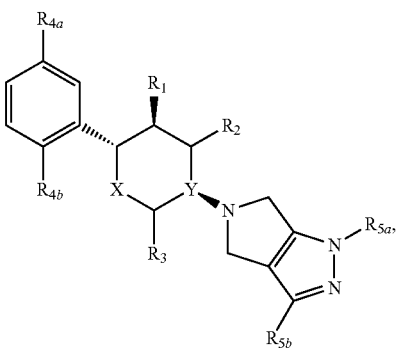

III wherein,
X is O;
Y is selected from the group consisting of N and CH;

$R_1$ is selected from the group consisting of —NH$_2$ and —OH;

both $R_2$ and $R_3$ are H;

$R_{4a}$ and $R_{4b}$ are each independently selected from the group consisting of F, Cl, Br, —NH$_2$ and —OH;

$R_{5a}$ and $R_{5b}$ are each independently selected from the group consisting of F, Cl, Br, I, —CN, —COOR$_6$, —NHR$_7$ and —SO$_2$R$_8$;

$R_6$ is selected from the group consisting of H, methyl, ethyl, propyl and butyl;

$R_7$ is selected from the group consisting of H, methyl, ethyl, propyl, butyl and —SO$_2$R$_8$; and each $R_8$ is independently selected from the group consisting of —OH, —NH$_2$, methyl, ethyl, propyl, butyl, C$_3$ cycloalkyl, C$_4$ cycloalkyl and C$_5$ cycloalkyl.

In another aspect, the present application provides a compound of formula IV or a pharmaceutically acceptable salt thereof:

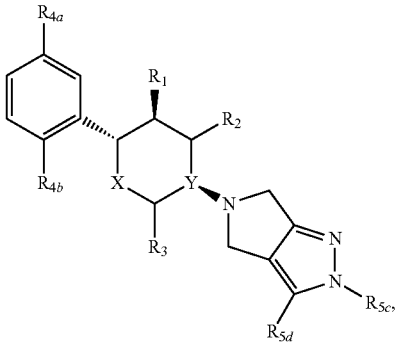

IV wherein
X is O;
Y is selected from the group consisting of N and CH;
$R_1$ is selected from the group consisting of —NH$_2$ and —OH;
$R_2$ and $R_3$ are both H;
$R_{4a}$ and $R_{4b}$ are each independently selected from the group consisting of F, Cl, Br, —NH$_2$ and —OH;
$R_{5c}$ and $R_{5d}$ together with the ring atom(s) of pyrazole to which they are attached form a 5, 6 or 7-membered non-aromatic ring, and the 5, 6 or 7-membered non-aromatic ring preferably contains 1, 2 or 3 heteroatoms selected from the group consisting of N, O and S, and the 5, 6 or 7-membered non-aromatic ring more preferably contains —SO$_2$— group.

In another aspect, the present application provides a compound of formula V or a pharmaceutically acceptable salt thereof:

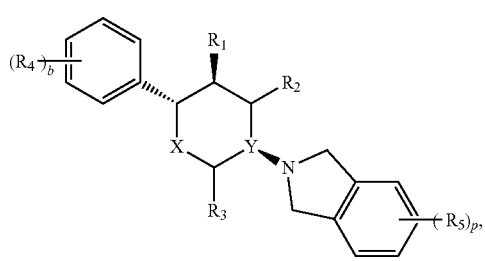

V wherein,
X is O;
Y is selected from the group consisting of N and CH;
$R_1$, $R_2$ and $R_3$ are each independently selected from the group consisting of H, C$_{1-3}$ alkyl, —NH$_2$ and —OH;
each $R_4$ is independently selected from the group consisting of halogen, —NH$_2$, —OH, C$_{1-6}$ alkyl, C$_{1-6}$ alkoxy, phenoxy and benzyloxy;
each $R_5$ is independently selected from the group consisting of C$_{1-6}$ alkyl, halogen, —CN, —OH, —COOR$_6$, —NHR$_7$ and —SO$_2$R$_8$;
$R_6$ is selected from the group consisting of H and C$_{1-6}$ alkyl;
$R_7$ is selected from the group consisting of H, C$_{1-6}$ alkyl and —SO$_2$R$_8$;
each $R_8$ is independently selected from the group consisting of —OH, —NH$_2$, C$_{1-6}$ alkyl and C$_{3-6}$ cycloalkyl; and
o and p are each independently 1, 2 or 3.

In one embodiment, in the compound of formula V, $R_1$ is preferably selected from the group consisting of —NH$_2$ and —OH.

In another embodiment, in the compound of formula V, $R_2$ and $R_3$ are preferably H.

In another embodiment, in the compound of formula V, $R_4$ is preferably selected from the group consisting of F, Cl, Br, I, —NH$_2$ and —OH.

In another embodiment, in the compound of formula V, $R_5$ is preferably selected from the group consisting of F, Cl, Br, I, —COOR$_6$, —NHR$_7$ and —SO$_2$R$_8$.

In another embodiment, in the compound of formula V, $R_6$ is preferably selected from the group consisting of H, methyl, ethyl, propyl and butyl.

In another embodiment, in the compound of formula V, $R_7$ is preferably selected from the group consisting of H, methyl, ethyl, propyl, butyl and —SO$_2$R$_8$.

In another embodiment, in the compound of formula V, $R_8$ is preferably selected from the group consisting of —OH, —NH$_2$, methyl, ethyl, propyl, butyl, C$_3$ cycloalkyl, C$_4$ cycloalkyl and C$_5$ cycloalkyl.

In another embodiment, in the compound of formula V, o is preferably 2.

In another embodiment, in the compound of formula V, p is preferably 1 or 2.

In another embodiment, in the compound of formula V, the substitution position of $R_4$ is preferably the positions of $R_{4a}$ and $R_{4b}$ as shown in the structure represented by the following formula VI:

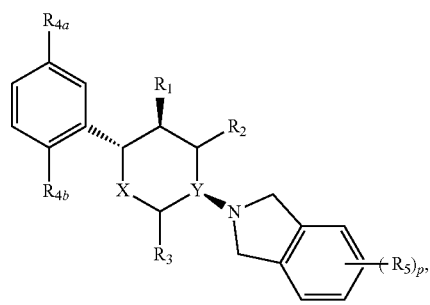

VI wherein $R_{4a}$ and $R_{4b}$ are each independently selected from the group consisting of F, Cl, Br, I, —NH$_2$ and —OH, and the remaining groups are defined the same as in formula V hereinbefore.

In another embodiment, in the compound of formula V, p is preferably 2, and the substitution position of $R_5$ is preferably the positions of $R_{5a}$ and $R_{5b}$ as shown in the structure represented by the following formula VII:

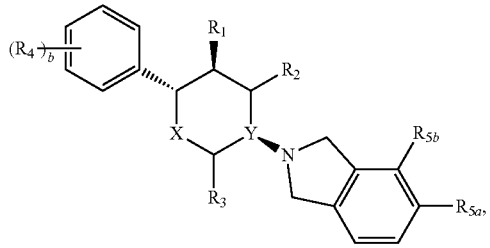

VII wherein $R_{5a}$ and $R_{5b}$ are each independently selected from the group consisting of F, Cl, Br, I, —COOR$_6$, —NHR$_7$ and —SO$_2$R$_8$, and other substituents are defined the same as in formula V hereinbefore.

In another embodiment, in the compound of formula V, p is preferably 1, and the substitution position of $R_5$ is preferably the position of $R_{5a}$ as shown in the structure represented by the following formula VIII:

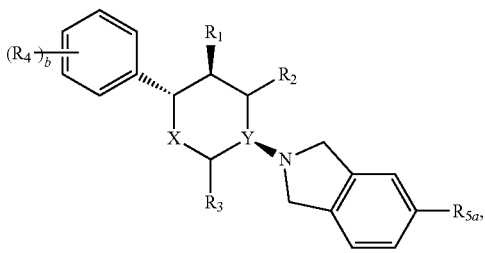

VIII wherein $R_{5a}$ is selected from the group consisting of F, Cl, Br, I, —COOR$_6$, —NHR$_7$ and —SO$_2$R$_8$, and other substituents are defined the same as in formula V hereinbefore.

The following compounds of the present application or pharmaceutically acceptable salts thereof are preferred.

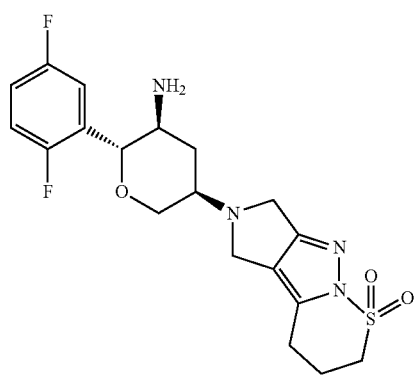

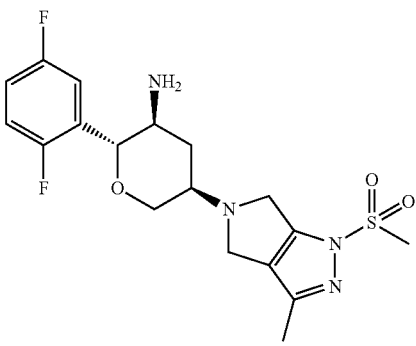

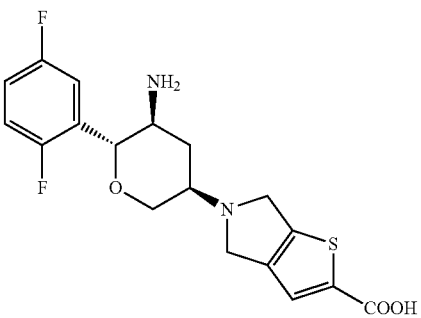

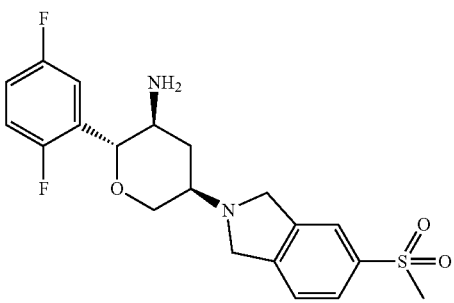

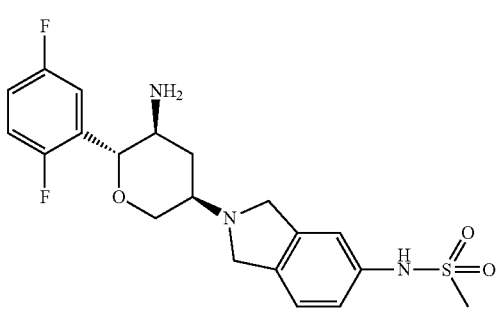

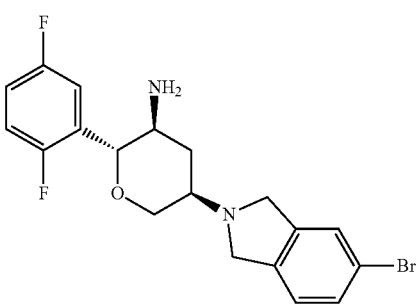

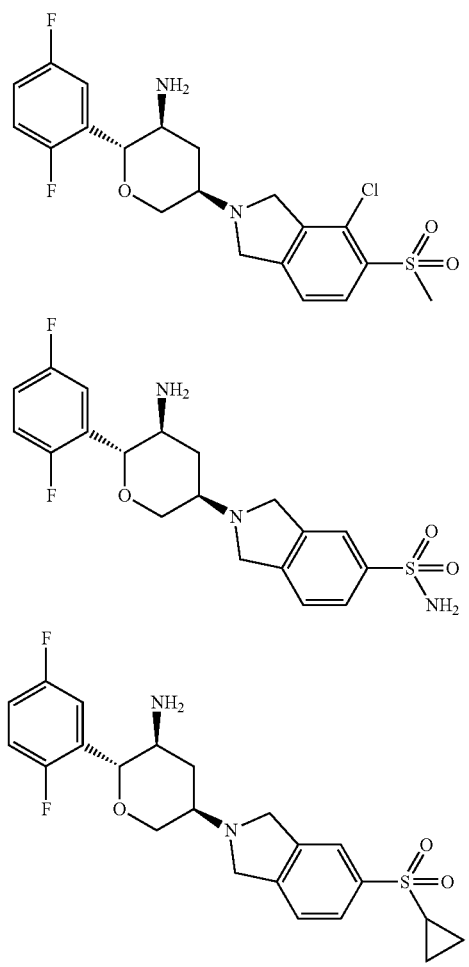

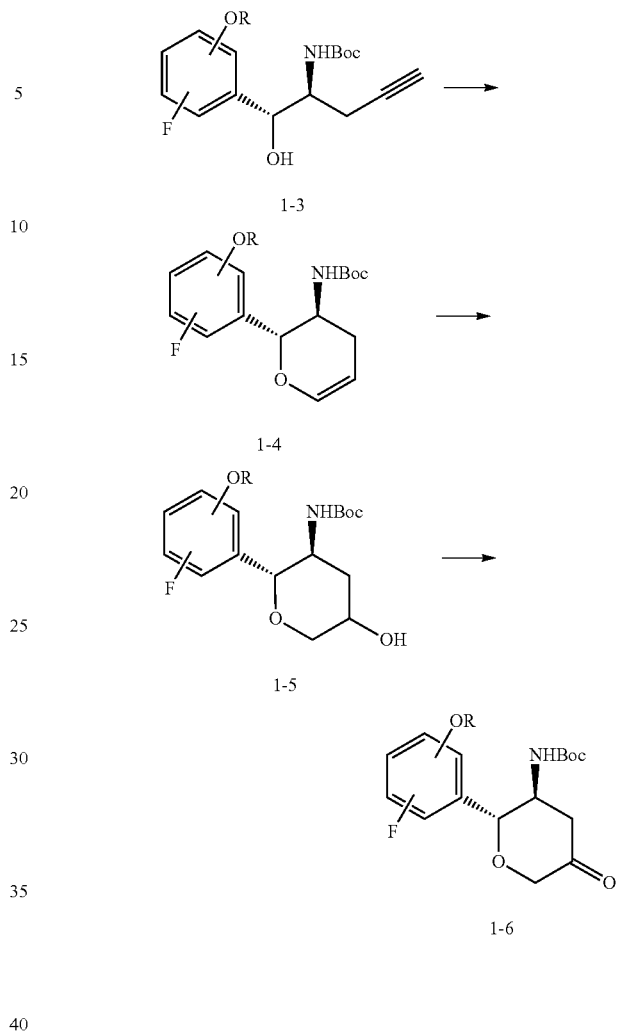

Process for Preparing Compounds of Formula I

In yet another aspect, the present application also provides a process for preparing the compounds of formula I, comprising the following synthesis schemes.

Synthesis Scheme 1

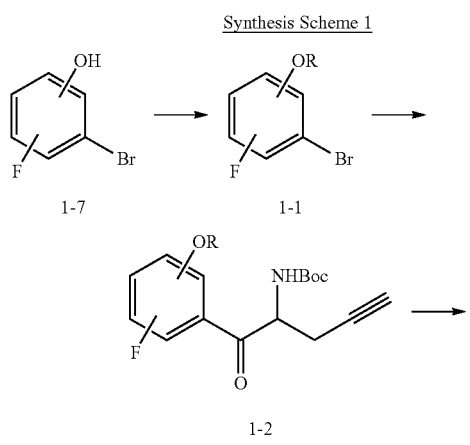

Compound 1-6 can be synthesized by using Synthesis Scheme 1. Halogenated phenol 1-7 is reacted with alkyl halide, benzyl halide or aryl halide (catalyzed by a metal) in the presence of a base to give halogenated aryl ether intermediate 1-1; intermediate 1-1 is metallized with a Grignard reagent and then reacted with Weinreb amide to give ketone intermediate 1-2; ketone intermediate 1-2 is selectively reduced by a chiral metal catalyst to give compound 1-3; intermediate 1-3 is subjected to a ring closing reaction catalyzed by a metal catalyst to give compound 1-4; the double bond in intermediate 1-4 is successively subjected to hydroboration reaction and oxidation reaction to obtain alcohol compound 1-5; and the alcoholic hydroxy group in intermediate 1-5 is catalytically oxidized to give compound 1-6.

Synthesis Scheme 2

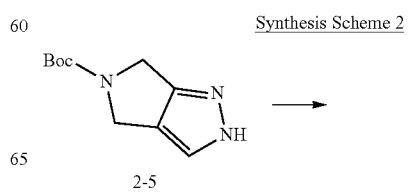

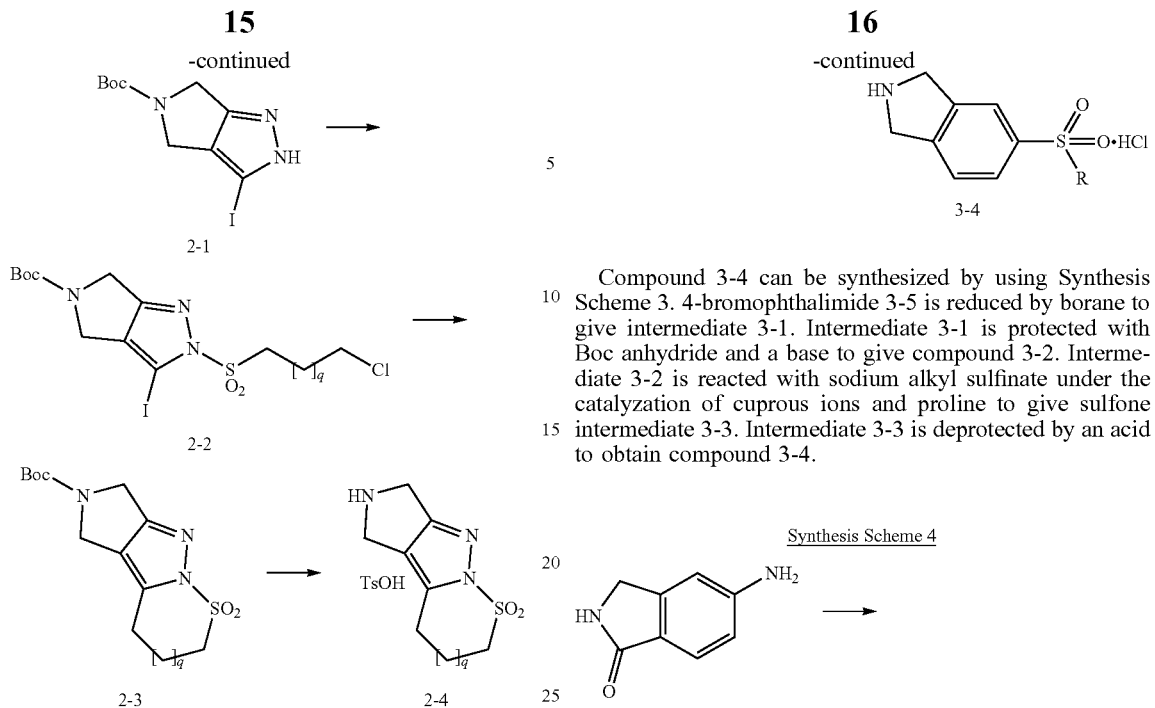

Compound 3-4 can be synthesized by using Synthesis Scheme 3. 4-bromophthalimide 3-5 is reduced by borane to give intermediate 3-1. Intermediate 3-1 is protected with Boc anhydride and a base to give compound 3-2. Intermediate 3-2 is reacted with sodium alkyl sulfinate under the catalyzation of cuprous ions and proline to give sulfone intermediate 3-3. Intermediate 3-3 is deprotected by an acid to obtain compound 3-4.

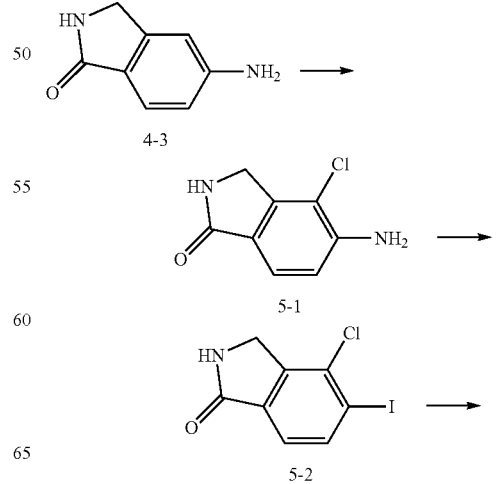

Compound 4-2 can be synthesized by using Synthesis Scheme 4. 5-amino-1-oxoisoindoline 4-3 is reacted with alkylsulfonyl chloride to give intermediate 4-1. Intermediate 4-1 is reduced by borane to give intermediate 4-2.

Compound 2-4 can be synthesized by using Synthesis Scheme 2 (q is 0, 1 or 2). Intermediate 2-5 is reacted with N-iodosuccinimide to give iodine-substituted intermediate 2-1. Intermediate 2-1 is reacted with chloroalkylsulfonyl chloride to give intermediate 2-2. Intermediate 2-2 is metallized with zinc powder and then is subjected to a metal-catalyzed ring closing reaction to give intermediate 2-3. Intermediate 2-3 can be deprotected by an acid to obtain compound 2-4.

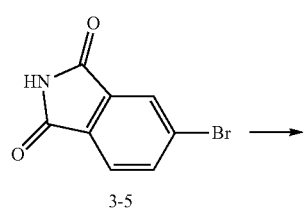

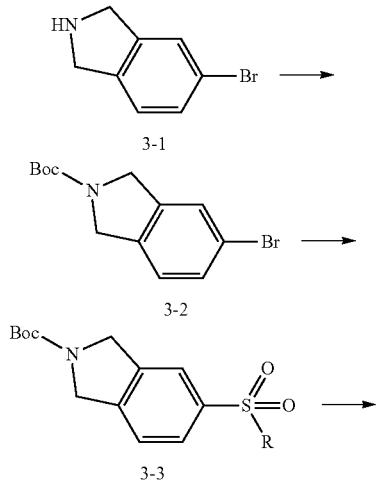

-continued

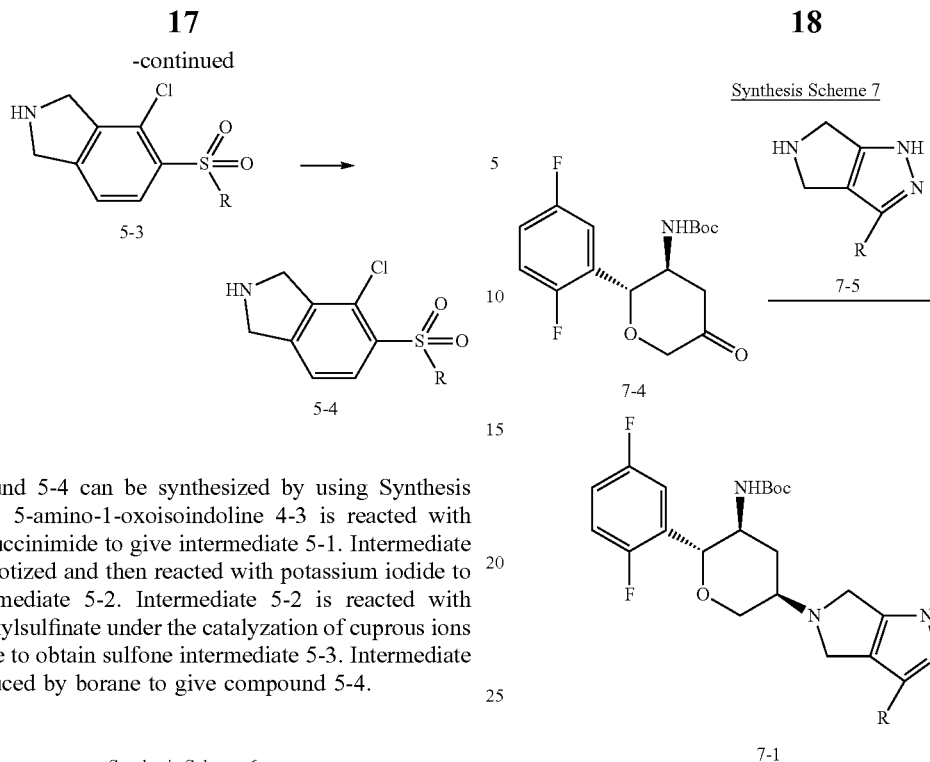

Compound 5-4 can be synthesized by using Synthesis Scheme 5. 5-amino-1-oxoisoindoline 4-3 is reacted with N-chlorosuccinimide to give intermediate 5-1. Intermediate 5-1 is diazotized and then reacted with potassium iodide to give intermediate 5-2. Intermediate 5-2 is reacted with sodium alkylsulfinate under the catalyzation of cuprous ions and proline to obtain sulfone intermediate 5-3. Intermediate 5-3 is reduced by borane to give compound 5-4.

Synthesis Scheme 6

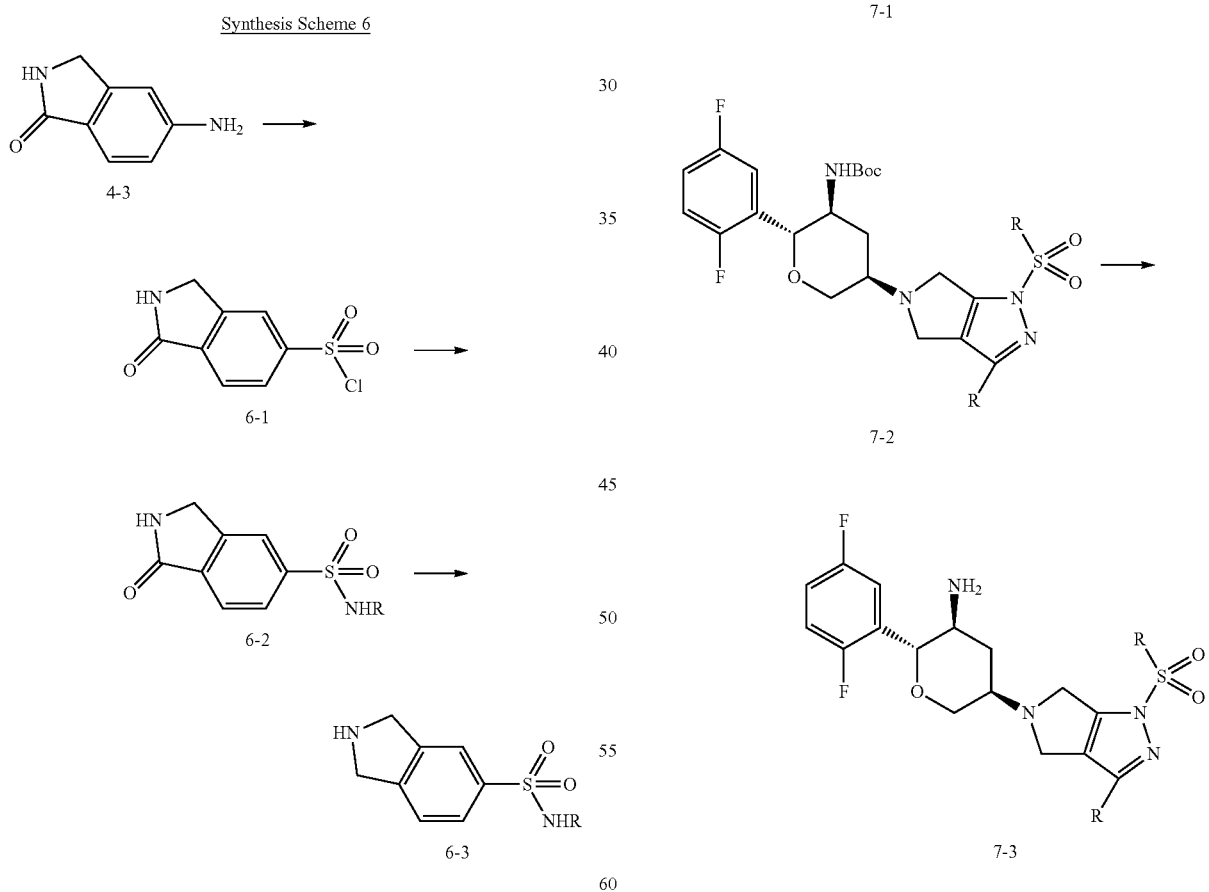

Compound 6-3 can be synthesized by using Synthesis Scheme 6. 5-amino-1-oxoisoindoline 4-3 is diazotized and then reacted with sulfur dioxide and cuprous chloride to give sulfonyl chloride intermediate 6-1. Intermediate 6-1 is reacted with an amine to give intermediate 6-2, which is then reduced by borane to give compound 6-3.

Compound 7-3 can be synthesized by using Synthesis Scheme 7. Ketone 7-4 is subjected to reductive amination with amine 7-5 to give intermediate 7-1, which is then reacted with alkylsulfonyl chloride to give intermediate 7-2. Intermediate 7-2 is deprotected under an acidic condition to obtain final compound 7-3.

Synthesis Scheme 8

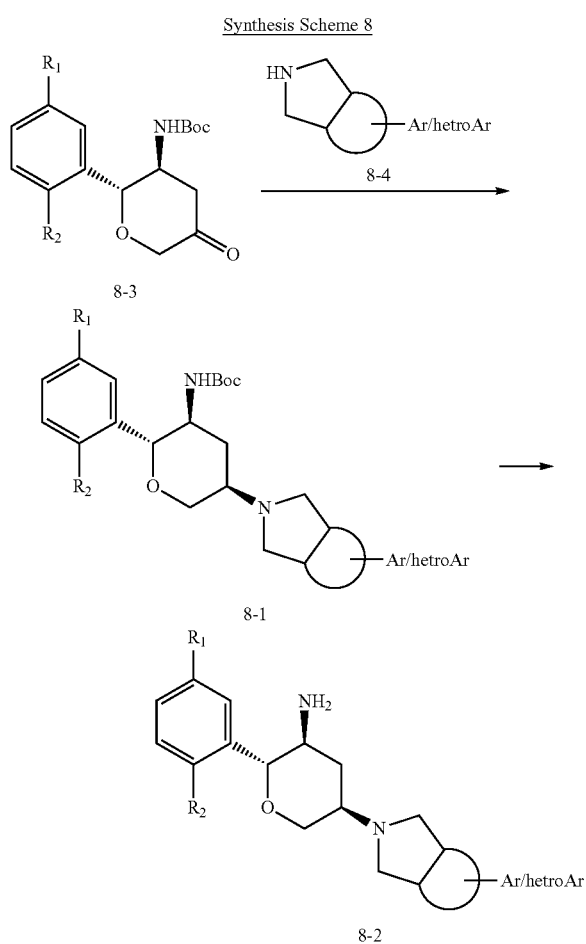

Compound 8-2 can be synthesized by using Synthesis Scheme 8. Ketone 8-3 is subjected to reductive amination with amine 8-4 to give intermediate 8-1. Intermediate 8-1 is deprotected under an acidic condition to obtain final compound 8-2.

The above synthesis schemes merely illustrate the preparation processes of parts of the compounds of the present application, and one of ordinary skill in the art can also use similar methods to synthesize the compounds of the present application on the basis of the above synthesis schemes.

Pharmaceutical Composition

The compounds of the present application or salts thereof may be administered alone as an active substance, preferably administered in the form of a pharmaceutical composition thereof.

In another aspect, the present application provides a pharmaceutical composition comprising a compound of formula I or a pharmaceutically acceptable salt, solvate, polymorph, metabolite thereof as an active ingredient, and one or more pharmaceutically acceptable carriers.

The compounds of the present application or pharmaceutically acceptable salts thereof may be administered in their pure forms or in the form of suitable pharmaceutical compositions through any acceptable administration routes of a medicament providing a similar use. The pharmaceutical compositions of the present application may be prepared by combining the compounds of the present application with a suitable pharmaceutically acceptable carrier, diluent, vehicle or excipient. The pharmaceutical compositions of the present application may be formulated into solid, semi-solid, liquid or gaseous formulations, such as tablets, pills, capsules, powders, granules, ointments, emulsions, suspensions, solutions, suppositories, injections, inhalants, gels, microspheres, aerosols, and the like.

Typical administration routes of the compounds of the present application or pharmaceutically acceptable salts thereof or pharmaceutical compositions thereof include, but are not limited to, oral, rectal, transmucosal, enteral administration, or local, transdermal, inhalation, parenteral, sublingual, intravaginal, intranasal, intraocular, intraperitoneal, intramuscular, subcutaneous, intravenous administration and the like. The preferred administration route is the oral administration.

The pharmaceutical compositions of the present application can be prepared by using methods well-known to those of ordinary skill in the art, such as conventional mixing method, dissolution method, granulation method, dragee manufacture method, grinding method, emulsification method, freeze-drying method, and the like.

In preferred embodiments, the pharmaceutical composition is in oral form. For oral administration, the pharmaceutical composition may be formulated by mixing the active compound(s) with pharmaceutically acceptable carrier(s) well-known in the art. Such a carrier enables the compounds of the present application to be formulated into tablets, pills, lozenges, dragees, capsules, liquids, gels, syrups, suspensions, and the like, for oral administration to patients.

A solid oral pharmaceutical composition can be prepared by a conventional mixing, filling or tabletting method. For example, it can be obtained by mixing the active compound with a solid excipient, optionally grinding the resulting mixture, adding other suitable excipients, if necessary, and then processing the mixture into granules to obtain tablets or cores of dragees. Suitable excipients include, but are not limited to, binders, diluents, disintegrants, lubricants, glidants, sweeting agents, flavoring agents, and the like, such as microcrystalline cellulose, glucose solution, acacia mucilage, gelatin solution, sucrose and starch paste; talc, starch, magnesium stearate, calcium stearate or stearic acid; lactose, sucrose, starch, mannitol, sorbitol or dicalcium phosphate; silica; croscarmellose sodium, pregelatinized starch, sodium starch glycolate, alginic acid, corn starch, potato starch, methylcellulose, agar, carboxymethyl cellulose, cross-linked polyvinylpyrrolidone, and the like. The cores of dragees may be optionally coated according to well-known methods in the pharmaceutical practice, in particular using an enteric coating.

The pharmaceutical compositions of the present application can also be suitable for parenteral administration, such as sterile solutions, suspensions or lyophilized products in a suitable unit dosage form. Suitable excipients, such as fillers, buffers or surfactants, can be used.

Therapeutic Use

In one aspect, the present application provides a use of a compound of formula I or a pharmaceutically acceptable salt, solvate, polymorph, metabolite thereof or a pharmaceutical composition thereof in the preparation of a medicament for the treatment of diseases and disorders benefitting from DPP-IV inhibition.

In yet another aspect, the present application provides a method for treating diseases and disorders benefitting from DPP-IV inhibition, comprising administering to a subject in need thereof a compound of formula I or a pharmaceutically acceptable salt, solvate, polymorph, metabolite thereof, or a pharmaceutical composition thereof.

In yet another aspect, the present application provides a compound of formula I or a pharmaceutically acceptable salt, solvate, polymorph, metabolite thereof or a pharmaceutical composition thereof for use in a method for the treatment of diseases and disorders benefitting from DPP-IV inhibition.

The diseases and disorders benefitting from DPP-IV inhibition are selected from the group consisting of insulin resistance, hyperglycemia, type II diabetes, diabetic dyslipidemia, impaired glucose tolerance (IGT), impaired fasting glucose (IFG), metabolic acidosis, ketosis, appetite regulation, obesity, various cancers, neurological disorders, immune system disorders, and the like, preferably type II diabetes or obesity.

The substituted amino six-membered heteroalicycle compounds provided by the present application have very good DPP-IV inhibitory activities, which are comparable to or better than that of Omarigliptin, have very good in vivo metabolism and very long in vivo half-lives, and are long-acting DPP-IV inhibitors.

Examples

The following specific examples are provided to enable those skilled in the art to more clearly understand and practice the invention. They should not be construed as limiting the scope of the invention, but as merely illustrations and typical representatives of the invention. Those skilled in the art would understand that there are other synthetic routes involved for preparing the compounds of the present application, and ones provided below are non-limiting examples.

All operations involving raw materials that are susceptible to oxidation or hydrolysis are carried out under a nitrogen protection atmosphere. Unless otherwise indicated, raw materials used in the present application are commercially available and directly used without further purification.

Column chromatography was performed using silica gel (200-300 mesh) produced by Qingdao Chemical Co., Ltd. Thin Layer Chromatography was performed using prefabricated plates (silica gel 60 $PF_{254}$, 0.25 mm) manufactured by E. Merck. Separation of chiral compounds and measurement of enantiomeric excess (ee) were performed using the Agilent LC 1200 series (column: CHIRALPAK AD-H, Ø4.6×250 mm, 5 microns, 30° C.). NMR spectrum was performed using Varian VNMRS-400 nuclear magnetic resonance spectrometer; and LC/MS was performed using FINNIGAN Thermo LCQ Advantage MAX, Agilent LC 1200 series (column: Waters Symmetry C18, Ø4.6×50 mm, 5 micron, 35° C.), and ESI (+) ion mode.

Intermediate 1: tert-butyl (2R,3 S)-2-(2,5-difluorophenyl)-5-oxotetrahydro-2H-pyran-3-ylcarbamate

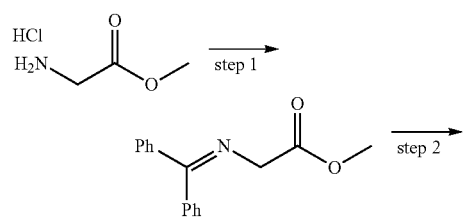

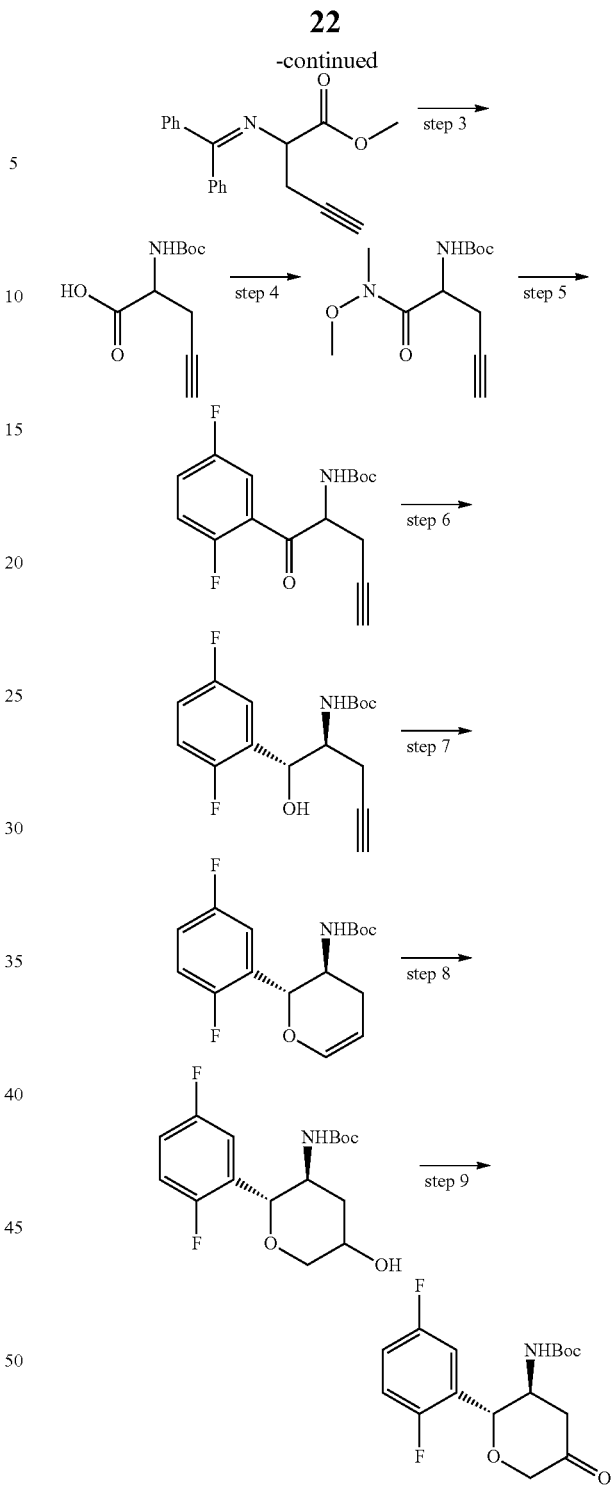

Step 1: methyl 2-((diphenylmethylene)amino)acetate

Benzophenone imine (50.0 g, 0.276 mol) was added in one batch to a solution of glycine methyl ester hydrochloride (39.4 g, 0.314 mol) in 300 mL dichloromethane under stirring, and the resulting reaction solution was stirred at room temperature for 1 day. The resulting solid was removed by filtration, and the filtrate was washed sequentially with water, sodium carbonate solution and saturated brine, and was concentrated by evaporation to give methyl 2-((diphenylmethylene)amino)acetate (64.2 g) as an oily product, which was solidified after being cooled, and used directly for next step. Yield: 92%. ¹H-NMR (400 MHz, CDCl₃): δ=7.66 (2H, m), 7.45 (4H, m), 7.35 (2H, m), 7.17 (2H, m), 4.22 (2H, s), 3.74 (3H, s).

Step 2: methyl 2-((diphenylmethylene)amino)pent-4-ynoate

To a solution of methyl 2-((diphenylmethylene)amino) acetate (64.2 g, 0.254 mol), propargyl bromide (27.8 mL, 0.322 mol) and tetra-n-butylammonium bromide (8.66 g, 26.9 mmol) in methyl tert-butyl ether (600 mL) was added cesium carbonate (175.4 g, 0.538 mol) under stirring. It was stirred at 50° C. for 2 days after addition. The resulting solid was removed by filtration, and the filter cake was washed with a small amount of methyl tert-butyl ether (MTBE), and the filtrate was concentrated to 300 mL and directly used for next step. ¹H-NMR (400 MHz, CDCl₃): δ=7.66 (2H, m), 7.45 (4H, m), 7.35 (2H, m), 7.17 (2H, m), 4.32 (1H, m), 3.73 (3H, s), 2.83 (2H, m), 1.95 (1H, s).

Step 3: 2-(tert-butoxycarbonylamino)pent-4-ynoic acid

To the concentrated solution obtained in the above step was added 280 mL of 1N hydrochloric acid, and stirred at room temperature until TLC showed that methyl 2-((diphenylmethylene)amino)pent-4-ynoate disappeared, which took about 12 hours. The organic phase was separated; the aqueous phase was extracted with methyl tert-butyl ether; and the organic phase was discarded. To the aqueous phase was added 50% sodium hydroxide solution (18.75 N, 0.712 mol) and stirred for 2 hours. Thereto were added 50 mL water and then a solution of Boc anhydride (61.0 g, 0.28 mol) in methyl tert-butyl ether (200 mL). The resulting mixture was stirred at room temperature for 6 hours, and acidified to pH 3 with 10% hydrochloric acid under an ice-bath cooling. The organic phase was separated, and the aqueous phase was extracted with methyl tert-butyl ether. The organic phases were combined, dried and concentrated to give the product 2-(tert-butoxycarbonylamino)pent-4-ynoic acid (38.8 g) with 72% total yield in two steps. ¹H-NMR (400 MHz, CDCl₃): δ=7.65 (1H, brs), 5.36 (1H, d, J=8.0 Hz), 4.52 (1H, m), 2.77 (2H, m), 2.08 (1H, s), 1.46 (9H, s).

Step 4: 2-(tert-butoxycarbonylamino)pent-4-ynylacyl-(N-methoxy-N-methyl)amine To a solution of 2-(tert-butoxycarbonylamino)pent-4-ynoic acid (20.22 g, 94.9 mmol) in acetonitrile (200 mL) were added 2-(7-azobenzotriazole)-N,N,N',N'-tetramethyluronium hexafluorophosphate (HATU) (43.27 g, 113.9 mmol), N,O-dimethylhydroxylamine hydrochloride (11.11 g, 113.9 mmol) and triethylamine (46.2 mL, 332.2 mmol), and stirred at room temperature for 2 hours. The reaction solution was poured into 1500 mL water, and extracted three times with ethyl acetate. The combined organic phase was washed sequentially with 1N hydrochloric acid, water, saturated sodium bicarbonate solution and saturated brine, dried and concentrated, and then the residue was purified by silica gel column chromatography (petroleum ether/ethyl acetate), 5:1 to 4:1) to give the product 2-(tert-butoxycarbonylamino) pent-4-ynylacyl-(N-methoxy-N-methyl)amine (19.6 g). Yield: 81%. ¹H-NMR (400 MHz, CDCl₃): δ=5.45 (1H, d, J=8.0 Hz), 4.82 (1H, m), 3.77 (3H, s), 3.24 (3H, s), 2.66 (2H, m), 2.04 (1H, s), 1.45 (9H, s).

Step 5: tert-butyl 1-(2,5-difluorophenyl)-1-oxopent-4-yn-2-ylcarbamate 2,5-difluorobromobenzene (11.58 g, 60 mmol) was dissolved in 25 mL toluene and cooled to −10° C. to 5° C. Thereto was added lithium bromide (2.61 g, 30 mmol), and a solution of isopropylmagnesium chloride in tetrahydrofuran (2 M, 33 ml, 66 mmol) was added dropwise over 1.5 hours, and stirred at low temperature for 1 hour. A solution of 2-(tert-butoxycarbonylamino)pent-4-ynylacyl-(N-methoxy-N-methyl)amine (7.68 g, 30 mmol) in 35 mL tetrahydrofuran was added dropwise to the reaction system over 1 hour, then slowly warmed to room temperature and stirred at room temperature for 1 hour. To a reaction solution was added 22 mL of 3N hydrochloric acid to quench the reaction. The organic phase was washed sequentially with water, saturated sodium bicarbonate solution and saturated brine, dried and concentrated, and the residue was purified by silica gel column chromatography (petroleum ether/ethyl acetate, 10:1) to give the product tert-butyl 1-(2,5-difluorophenyl)-1-oxopent-4-yn-2-ylcarbamate (6.07 g). Yield: 65%. ¹H-NMR (400 MHz, CDCl₃): δ=7.56 (1H, m), 7.26 (1H, m), 7.15 (1H, m), 5.68 (1H, d, J=7.6 Hz), 5.24 (1H, m), 2.91 (1H, m), 2.68 (1H, m), 1.99 (1H, s), 1.45 (9H, s).

Step 6: tert-butyl (1R,2S)-1-(2,5-difluorophenyl)-1-hydroxylpent-4-yn-2-ylcarbamate 1-(2,5-difluorophenyl)-1-oxopent-4-yn-2-ylcarbamate (6.07 g, 19.7 mmol) and 1,4-diazabicyclo[2.2.2]octane (DABCO) (6.61 g, 59 mmol) were dissolved in 70 mL tetrahydrofuran, and purged with nitrogen for 30 minutes. ((1R,2R)—N-p-toluenesulfonyl-1,2-diphenylethylenediamine) ruthenium chloride (I) (4-cymene) (63 mg, 0.1 mmol) was added, and purged with nitrogen/vacuumized three times. Formic acid (4.53 g, 98.5 mmol) was added dropwise to the reaction solution under nitrogen atmosphere, and stirred at 40° C. for 2 days. 200 mL dichloromethane was added, and then washed sequentially with 5% citric acid solution, saturated sodium bicarbonate solution and saturated brine, dried and concentrated, and then the residue was purified by silica gel column chromatography (petroleum ether/ethyl acetate, 25:1-8:1) to give the product tert-butyl (1R,2S)-1-(2,5-difluorophenyl)-1-hydroxylpent-4-yn-2-ylcarbamate (6.11 g). Yield: 100%.

Step 7: tert-butyl (2R,3S)-2-(2,5-difluorophenyl)-3,4-dihydro-2H-pyran-3-ylcarbamate Tert-butyl (1R,2S)-1-(2,5-difluorophenyl)-1-hydroxylpent-4-yn-2-ylcarbamate (6.11 g, 19.6 mmol) was dissolved in 60 mL DMF, and purged with nitrogen for 30 minutes. Tris(tris(3-fluorophenyl)phosphine) rhodium chloride catalyst (427 mg, 0.393 mmol) was added, purged with nitrogen/vacuumized three times, and stirred at 80° C. for 16 hours under nitrogen atmosphere. After cooling, 150 mL water and 150 mL saturated sodium bicarbonate solution were added, and extracted with toluene. The combined organic phase was washed several times with water, dried and concentrated, and then the residue was purified ny silica gel column chromatography (petroleum ether/ethyl acetate, 30:1-25:1) to give the product tert-butyl (2R,3 S)-2-(2,5-difluorophenyl)-3,4-dihydro-2H-pyran-3-ylcarbamate (4.89 g). Yield: 80%.

Step 8: tert-butyl (2R,3S)-2-(2,5-difluorophenyl)-5-hydroxyltetrahydro-2H-pyran-3-ylcarbamate Tert-butyl (2R,3 S)-2-(2,5-difluorophenyl)-3,4-dihydro-2H-pyran-3-ylcarbamate (2.81 g, 9.04 mmol) was dissolved in 50 mL of tetrahydrofuran and cooled to −10° C. Borane-dimethyl sulfide complex (2.26 mL, 22.6 mmol) was added dropwise, stirred at low temperature for 2 hours and then warmed to 15° C. To the solution was added 1N sodium hydroxide solution (27.1 mL, 27.1 mmol) and sodium perborate (4.17 g, 27.1 mmol), and stirred overnight. 100 mL water was added. The organic phase was separated, and the aqueous phase was extracted with dichloromethane. The organic phases were combined, washed with water, dried and concentrated, and then the residue was purified by silica gel column chromatography (dichloromethane/methanol, 30:1-12:1) to give the product tert-butyl (2R,3 S)-2-(2,5-difluorophenyl)-5-hydroxyltetrahydro-2H-pyran-3-yl carbamate (2.33 g) as a white solid in 78% yield.

Step 9: tert-butyl (2R,3 S)-2-(2,5-difluorophenyl)-5-oxotetrahydro-2H-pyran-3-ylcarbamate Tert-butyl (2R,3 S)-2-(2,5-difluorophenyl)-5-hydroxyltetrahydro-2H-pyran-3-ylcarbamate (2.33 g, 7.08 mmol) was dissolved in a mixed solution of 24 mL acetonitrile, 4 mL water and 4 mL acetic acid. Thereto was added an aqueous solution (4 mL) of ruthenium chloride hydrate (3.7 mg, 0.0142 mmol), and cooled to 0° C. Sodium bromate (535 mg, 3.54 mmol) was added, and stirred at low temperature for about 1.5 hours until the raw materials were completely reacted. To the reaction solution was added 120 mL water, stirred at 0° C. overnight, and extracted with dichloromethane. The organic phase was washed with water, dried and concentrated, and then the residue was purified by silica gel column chromatography (petroleum ether/ethyl acetate, 10:1) to give the intermediate 1 tert-butyl (2R,3S)-2-(2,5-difluorophenyl)-5-oxotetrahydro-2H-pyran-3-ylcarbamate (1.71 g) as a white solid in 74% yield. $^1$H-NMR (400 MHz, CDCl$_3$): δ=7.22 (1H, m), 7.00 (1H, m), 4.82 (1H, m), 4.63 (1H, m), 4.29 (1H, d, J=16.2 Hz), 4.11 (1H, d, J=16.4 Hz), 4.05 (1H, m), 3.05 (1H, m), 2.85 (1H, m), 1.30 (9H, s).

Intermediate 2: 2,3,4,5,6,7-hexahydropyrrolo[3',4':3,4]pyrazolo[1,5-b][1,2]thiazine-1,1-dioxide p-toluenesulfonate

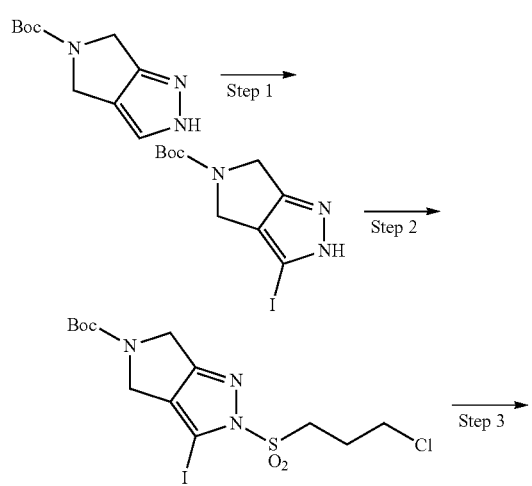
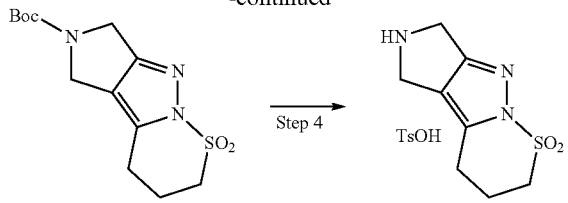

Step 1: tert-butyl 3-iodo-4,6-dihydropyrrolo[3,4-c]pyrazole-5(2H)-carboxylate To a solution of tert-butyl 4,6-dihydropyrrolo[3,4-c]pyrazole-5(2H)-carboxylate (9.41 g, 45 mmol) in 200 mL 1,2-dichloroethane was added N-iodosuccinimide (13.16 g, 58.5 mmol), and refluxed overnight. The solvent was removed by evaporation, and the residue was purified by silica gel column chromatography to give tert-butyl 3-iodo-4,6-dihydropyrrolo[3,4-c]pyrazole-5(2H)-carboxylate (4.66 g). Yield: 31%. MS m/z[ESI]: 336.0[M+1].

Step 2: tert-butyl 2-(3-chloropropylsulfonyl)-3-iodo-4,6-dihydropyrrolo[3,4-c]pyrazole-5(2H)-carboxylate Tert-butyl 3-iodo-4,6-dihydropyrrolo[3,4-c]pyrazole-5(2H)-carboxylate (2.80 g, 8.36 mmol) and triethylamine (1.69 g, 16.7 mmol) were dissolved in 80 mL tetrahydrofuran, and cooled to −10° C. Thereto was added 3-chloropropylsulfonyl chloride (1.77 g, 10 mmol), and stirred at low temperature overnight. Water (100 mL) was added, and extracted with dichloromethane. The organic phase was washed sequentially with citric acid solution, water, and brine, dried and concentrated by evaporation, and then the residue was purified by silica gel column chromatography to give tert-butyl 2-(3-chloropropylsulfonyl)-3-iodo-4,6-dihydropyrrolo [3,4-c]pyrazole-5(2H)-carboxylate (2.70 g). Yield: 68%. $^1$H-NMR (400 MHz, CDCl$_3$): δ=4.675 (2H, m), 4.35 (2H, m), 3.68 (4H, m), 2.26 (2H, m), 1.51 (9H, s).

Step 3: 6-tert-butoxycarbonyl-2,3,4,5,6,7-hexahydropyrrolo[3',4':3,4]pyrazolo[1,5-b][1,2]thiazine-1,1 dioxide Tert-butyl 2-(3-chloropropylsulfonyl)-3-iodo-4,6-dihydropyrrolo[3,4-c]pyrazole-5(2H)-carboxylate (230 mg, 0.48 mmol), zinc powder (126 mg, 1.93 mmol), a solution of zinc chloride in tetrahydrofuran (0.5 M, 1.93 mL, 0.97 mmol) and tetrahydrofuran (20 mL) were added into a microwave reaction tube, and purged with nitrogen for 5 minutes. The reaction was carried out under nitrogen atmosphere at 100° C. by microwave heating for 1.5 hours. After cooling, tetrakis (triphenylphosphine) palladium (56 mg, 0.048 mmol) was added, and purged with nitrogen for 5 minutes. The reaction was carried out under nitrogen atmosphere at 100° C. by microwave heating for 2 hours. After filtration, the filtrate was evaporated and concentrated, and then the residue was separated by silica gel column chromatography to give the product 6-tert-butoxycarbonyl-2,3,4,5,6,7-hexahydropyrrolo[3',4':3,4]pyrazolo[1,5-b][1,2]thiazine-1,1-dioxide (23 mg). Yield: 15%. MS m/z [ESI]: 314.1[M+1]. $^1$H-NMR (400 MHz, CDCl$_3$): δ=4.36 (2H, m), 4.11 (2H, m), 3.70 (2H, m), 3.35 (2H, m), 2.26 (2H, m), 1.47 (9H, s).

Step 4: 2,3,4,5,6,7-hexahydropyrrolo[3',4':3,4]pyrazolo[1,5-b][1,2]thiazine-1,1-dioxide p-toluenesulfonate To a solution of 6-tert-butoxycarbonyl-2,3,4,5,6,7-hexahydropyrrolo[3',4':3,4]pyrazolo[1,5-b][1,2]thiazine-1,1-dioxide (46 mg, 0.15 mmol) in 1.5 mL ethyl acetate was added p-toluenesulfonic acid (47 mg, 0.30 mmol), and stirred at room temperature overnight. The resulting solid was collected by filtration, washed with ethyl acetate, and dried to give the product 2,3,4,5,6,7-hexahydropyrrolo[3',4':3,4]pyrazolo[1,5-b][1,2]thiazine-1,1-dioxide p-toluenesulfonate (48 mg). Yield: 83%. MS m/z[ESI]: 214.1[M+1]. $^1$H-NMR (400 MHz, DMSO-$d_6$): δ=9.40 (2H, brs), 7.48 (2H, d, J=8.0 Hz), 7.12 (2H, d, J=8.0 Hz), 4.27 (2H, s), 4.08 (2H, s), 3.77 (2H, t, J=6.6 Hz), 3.45 (2H, t, J=7.4 Hz), 2.29 (3H, s), 2.16 (2H, m).

Intermediate 3: 3-methyl-2,4,5,6-tetrahydropyrrolo[3,4-c]pyrazole

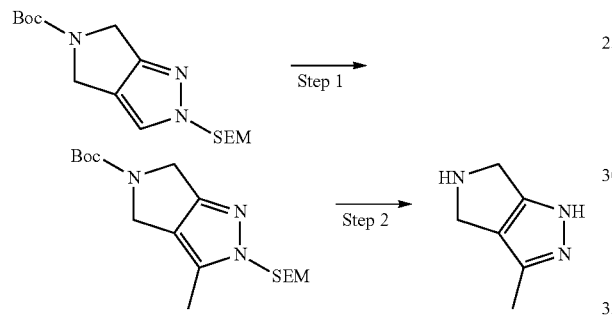

Step 1: tert-butyl 3-methyl-2-((2-(trimethylsilyl)ethoxy)methyl)-4,6-dihydropyrrolo[3,4-c]pyrazole-5(2H)-carboxylate Tert-butyl 2-((2-(trimethylsilyl)ethoxy)methyl)-4,6-dihydropyrrolo[3,4-c]pyrazole-5 (2H)-carboxylate (3.0 g, 8.85 mmol) was dissolved in dried tetrahydrofuran (60 mL), and cooled to −78° C. Thereto was added dropwise a solution of n-butyl lithium in tetrahydrofuran (2.4 M, 5.5 mL, 13.2 mmol), and stirred at low temperature for 1.5 hours. Methyl iodide (1.90 g, 13.2 mmol) was added dropwise, stirred at low temperature for 5 hours, and then warmed to room temperature. Water (50 mL) was added, and extracted with ethyl acetate. The organic phase was dried, evaporated, and concentrated, and then the residue was purified by silica gel column chromatography to give tert-butyl 3-methyl-2-((2-(trimethylsilyl)ethoxy)methyl)-4,6-dihydropyrrolo[3,4-c]pyrazole-5(2H)-carboxylate (1.5 g). Yield: 48%. MS m/z [ESI]: 354.2[M+1].

Step 2: 3-Methyl-2,4,5,6-tetrahydropyrrolo[3,4-c]pyrazole

To a solution of tert-butyl 3-methyl-2-((2-(trimethyl silyl)ethoxy)methyl)-4,6-dihydropyrrolo [3,4-c]pyrazole-5(2H)-carboxylate (1.1 g, 3.12 mmol) in 20 mL ethanol was added 1N hydrochloric acid (40 mL), and reacted in a sealed tube at 90° C. for 3 hours. After cooling, the pH was adjusted to 13 with sodium hydroxide solution. The resulting mixture was concentrated, and then the residue was purified by silica gel column chromatography to give the product 3-methyl-2,4,5,6-tetrahydropyrrolo[3,4-c]pyrazole (280 mg). Yield: 73%. MS m/z[ESI]: 124.1[M+1].

Intermediate 4: 5-methylsulfonylisoindoline hydrochloride

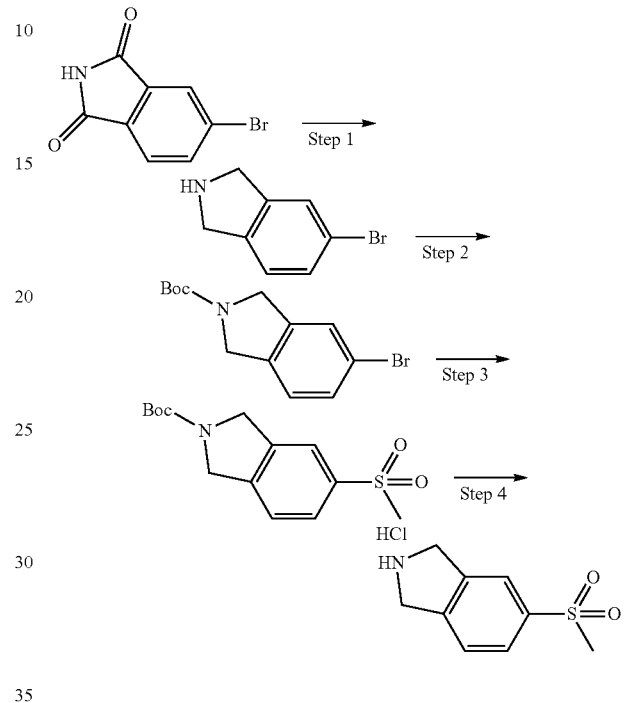

Step 1: 5-bromoisoindoline

To a solution of 4-bromophthalimide (22.6 g, 100 mmol) in dried tetrahydrofuran (250 mL) was added dropwise borane-dimethyl sulfide complex (51 mL, 500 mmol), stirred at room temperature for 2 hours, and then refluxed overnight. After cooling, methanol was carefully added dropwise to quench the excess borane. The resulting mixture was evaporated and concentrated, and then the residue was purified by silica gel column chromatography to give 5-bromoisoindoline (10.36 g). Yield: 52%. MS m/z[ESI]: 198.0 [M+1].

Step 2: 5-bromo-2-tert-butoxycarbonylisoindoline

5-Bromoisoindoline (10.36 g, 52.3 mmol) was dissolved in 80 mL dichloromethane, and cooled in an ice bath. Boc anhydride (22.8 g, 104.6 mmol) was added dropwise followed by the addition of sodium carbonate (16.6 g, 156.9 mmol) and water (150 mL), and stirred in an ice bath for 4 hours. The organic phase was separated, washed with brine, and concentrated, and then the residue was purified by silica gel column chromatography to give the product 5-bromo-2-tert-butoxycarbonylisoindoline (13.3 g). Yield: 85%. MS m/z [ESI]: 298.0[M+1]. $^1$H-NMR (400 MHz, CDCl$_3$): δ=7.37 (2H, m), 7.11 (1H, m), 4.62 (4H, m), 1.51 (9H, s).

Step 3: 5-methylsulfonyl-2-tert-butoxycarbonylisoindoline

5-Bromo-2-tert-butoxycarbonylisoindoline (5.96 g, 20 mmol), sodium methylsulfinate (90%, 2.94 g, 26 mmol), cuprous iodide (762 mg, 4 mmol) and L-proline (920 mg, 8 mmol) were added to dimethylsulfoxide (80 mL), purged with nitrogen to remove air, and stirred at 120° C. for 2 days. After cooling, the resulting mixture was poured into water and extracted with ethyl acetate. The organic phase was dried, evaporated, and concentrated, and then the residue was purified by silica gel column chromatography to give 5-methylsulfonyl-2-tert-butoxycarbonylisoindoline (5.46 g). Yield: 92%. MS m/z [ESI]: 298.1 [M+1].

Step 4: 5-methylsulfonylisoindoline hydrochloride

A solution of 5-methylsulfonyl-2-tert-butoxycarbonylisoindoline (5.46 g, 18.4 mmol) in methanol/dichloromethane (1:1, 80 mL) was purged with hydrogen chloride gas until saturation, and stirred at room temperature for 1 hour. After the resulting mixture was poured into 800 mL ethyl ether, the precipitate was collected by filtration, washed with ethyl ether and dried to give the product 5-methylsulfonylisoindoline hydrochloride (3.44 g). Yield: 80%. MS m/z[ESI]: 198.0[M+1]. $^1$H-NMR (400 MHz, CDCl$_3$): δ=7.82 (1H, s), 7.81 (1H, d, J=8.0 Hz), 7.43 (1H, d, J=8.0 Hz), 4.31 (4H, s), 3.05 (3H, s), 2.30 (2H, brs).

Intermediate 5: 5-methylsulfonamidoisoindoline

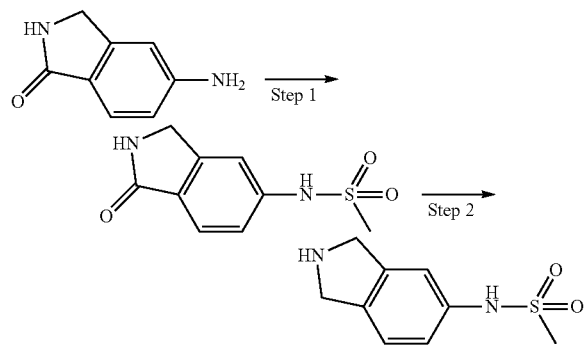

Step 1: 1-oxo-5-methylsulfonamidoisoindoline

To a solution of 5-aminoisoindolin-1-one (444 mg, 3 mmol) in 15 mL pyridine was added methylsulfonyl chloride (378 mg, 3.3 mmol), and stirred at room temperature for 4 hours. After the evaporation of the solvent, 1-oxo-5-methylsulfonamidoisoindoline (610 mg) was obtained by silica gel column chromatography. Yield: 90%. MS m/z [ESI]: 227.0 [M+1].

Step 2: 5-methylsulfonamidoisoindoline

To a solution of 1-oxo-5-methylsulfonamidoisoindoline (610 mg, 2.7 mmol) in tetrahydrofuran (10 mL) was added a solution of borane in tetrahydrofuran (1 M, 8.1 mL, 8.1 mmol), stirred at room temperature for 2 hours and then refluxed overnight. After cooling, methanol was carefully added dropwise to quench the excess borane. The resulting mixture was evaporated, concentrated and then purified by silica gel column chromatography to give 5-methylsulfonamidoisoindoline (315 mg). Yield: 55%. MS m/z [ESI]: 213.1[M+1].

Intermediate 6:
4-chloro-5-methylsulfonylisoindoline

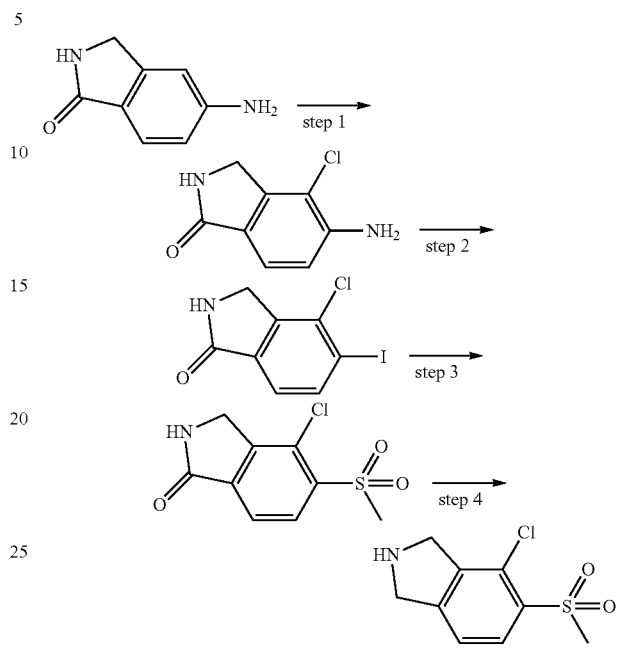

Step 1: 4-chloro-5-aminoisoindolin-1-one

To a solution of 5-aminoisoindolin-1-one (2.96 g, 20 mmol) in chloroform (50 mL) was added N-chlorosuccinimide (2.67 g, 20 mmol), and stirred under reflux for 2 hours. The resulting mixture was evaporated, concentrated and then purified by silica gel column chromatography to give 4-chloro-5-aminoisoindolin-1-one (2.58 g). Yield: 70%. MS m/z[ESI]: 183.0[M+1].

Step 2: 4-chloro-5-iodoisoindolin-1-one 4-chloro-5-aminoisoindolin-1-one (2.58 g, 14 mmol) was added to 15 mL of 2M sulfuric acid, and cooled in an ice bath. A solution of sodium nitrite (0.97 g, 28 mmol) in water (1.5 mL) was added dropwise, and stirred at low temperature for 30 mins. Potassium iodide (11.62 g, 70 mmol) was added, stirred in an ice bath for 2 hours, and then stirred at room temperature for 2 hours. The resulting mixture was extracted with dichloromethane, and the organic phase was washed with water and then brine. After concentration, the product 4-chloro-5-iodoisoindolin-1-one (2.48 g) was obtained by silica gel column chromatography. Yield: 60%. MS m/z[ESI]: 293.9[M+1]. $^1$H-NMR (400 MHz, CDCl$_3$): δ=8.01 (1H, d, J=8.0 Hz), 7.49 (1H, d, J=8.0 Hz), 4.44 (4H, m).

Step 3: 4-chloro-5-methylsulfonylisoindolin-1-one 4-chloro-5-iodoisoindolin-1-one (1.76 g, 6 mmol), sodium methylsulfinate (90%, 0.884 g, 7.8 mmol), cuprous iodide (229 mg, 1.2 mmol) and L-proline (276 mg, 2.4 mmol) were added to dimethylsulfoxide (25 mL), purged with nitrogen to remove air, and stirred at 110° C. for 2 days. After cooling, the resulting mixture was poured into water and extracted with ethyl acetate. The organic phase was dried, evaporated, and concentrated, and then the residue was purified by silica gel column chromatography to give 4-chloro-5-methylsulfonylisoindolin-1-one (1.03 g). Yield: 70%. MS m/z[ESI]:246.0[M+1].

Step 4: 4-chloro-5-methylsulfonylisoindoline

To a solution of 4-chloro-5-methylsulfonylisoindolin-1-one (249 mg, 1 mmol) in tetrahydrofuran (10 mL) was added a solution of borane in tetrahydrofuran (1M, 4 mL, 4 mmol), stirred at room temperature for 2 hours and then stirred under reflux overnight. After cooling, methanol was carefully added dropwise to quench the excess borane. The resulting mixture was evaporated, concentrated and then purified by silica gel column chromatography to give 4-chloro-5-methylsulfonylisoindoline (170 mg). Yield: 73%. MS m/z [ESI]: 232.0[M+1]. $^1$H-NMR (400 MHz, CDCl$_3$): δ=8.08 (1H, d, J=8.0 Hz), 7.32 (1H, d, J=8.0 Hz), 4.30 (4H, m), 3.32 (3H, s), 2.80 (1H, brs).

Intermediate 7: isoindoline-5-sulfonamide

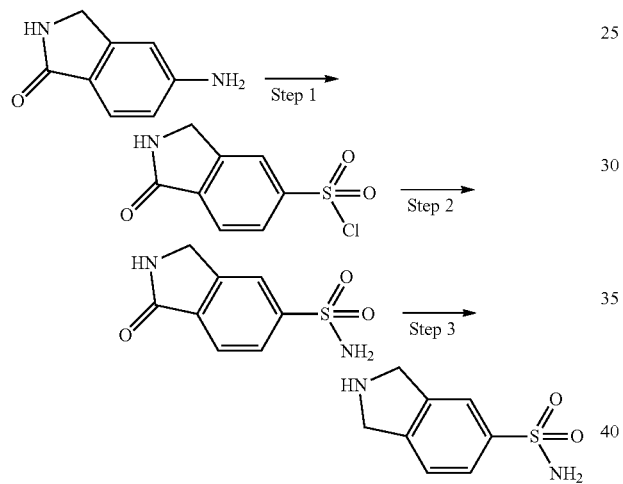

Step 1: 1-oxoisoindoline-5-sulfonyl chloride

5-Aminoisoindolin-1-one (5.92 g, 40 mmol) was added to a mixed solvent of concentrated hydrochloric acid/glacial acetic acid (13.3/4.0 mL), and cooled in an ice bath. A solution of sodium nitrite (3.04 g, 28 mmol) in water (4.4 mL) was added dropwise, and stirred at low temperature for 30 minutes. At the same time, glacial acetic acid was added in another flask and purged with sulfur dioxide until saturation. Thereto was added cuprous chloride (0.99 g, 10 mmol), and continuously purged with sulfur dioxide under stirring until the solid was almost completely dissolved. Diazonium salt solution prepared above was added dropwise slowly, and stirred at low temperature for half an hour and then at room temperature for 1 hour. The resulting mixture was extracted with dichloromethane, washed with water, and dried to give 1-oxoisoindoline-5-sulfonyl chloride (8.33 g). Yield: 90%. MS m/z[ESI]: 232.0[M+1].

Step 2: 1-oxoisoindoline-5-sulfonamide

1-Oxoisoindoline-5-sulfonyl chloride (463 mg, 2 mmol) was added to 20 mL acetonitrile. Concentrated ammonia (1 mL, 12 mmol) was added dropwise, and stirred for 3 hours. The reaction solution was neutralized with 6N hydrochloric acid until the pH was neutral. After acetonitrile was removed via spin-evaporation, the residue was filtrated after the addition of water, and the filtrate cake was washed with water and ethyl acetate, and dried to give the product 1-oxoisoindoline-5-sulfonamide (288 mg). Yield: 68%. MS m/z [ESI]: 213.0[M+1].

Step 3: isoindoline-5-sulfonamide

To a solution of 1-oxoisoindoline-5-sulfonamide (288 mg, 1.36 mmol) in tetrahydrofuran (15 mL) was added a solution of borane in tetrahydrofuran (1M, 6.8 mL, 6.8 mmol), and stirred at room temperature for 2 hours and then stirred under reflux overnight. After cooling, methanol was carefully added dropwise to quench the excess borane. The resulting mixture was evaporated, concentrated and then purified by silica gel column chromatography to give isoindoline-5-sulfonamide (162 mg). Yield: 60%. MS m/z[ESI]: 199.0[M+1].

Intermediate 8: 5-cyclopropylsulfonylisoindoline hydrochloride

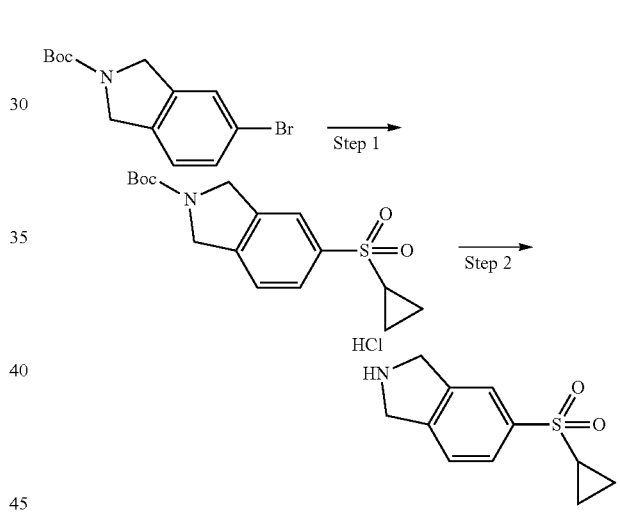

Step 1: 5-cyclopropylsulfonyl-2-tert-butoxycarbonylisoindoline

5-Bromo-2-tert-butoxycarbonylisoindoline (2.98 g, 10 mmol), sodium cyclopropylsulfinate (90%, 1.85 g, 13 mmol), cuprous iodide (381 mg, 2 mmol) and L-proline (460 mg, 4 mmol) were added to dimethylsulfoxide (40 mL), purged with nitrogen to remove air, and stirred at 110° C. for 2 days. After cooling, the resulting mixture was poured into water and extracted with ethyl acetate. The organic phase was dried, evaporated, and concentrated, and then the residue was purified by silica gel column chromatography to give 5-cyclopropylsulfonyl-2-tert-butoxycarbonylisoindoline (2.30 g). Yield: 71%. MS m/z[ESI]: 324.1[M+1].

Step 2: 5-cyclopropylsulfonylisoindoline hydrochloride 5-cyclopropylsulfonyl-2-tert-butoxycarbonylisoindoline (2.30 g, 7.1 mmol) was dissolved in methanol/dichloromethane (1:1, 40 mL), purged with hydrogen chloride gas until saturation, and stirred at room temperature for 2 hours. After the resulting mixture was poured into 250 mL ethyl ether, the precipitate was collected by filtration, washed with ethyl ether and dried to give the product 5-cyclopropylsulfonylisoindoline hydrochloride (1.85 g). Yield: 100%. MS m/z[ESI]: 224.1[M+1].

Example 1: (2R,3S,5R)-5-(2,3,4,5,6,7-hexahydropyrrolo[3',4':3,4]pyrazolo[1,5-b][1,2]thiazine-1,1-dioxide-6-yl)-2-(2,5-difluorophenyl)tetrahydro-2H-pyran-3-amine

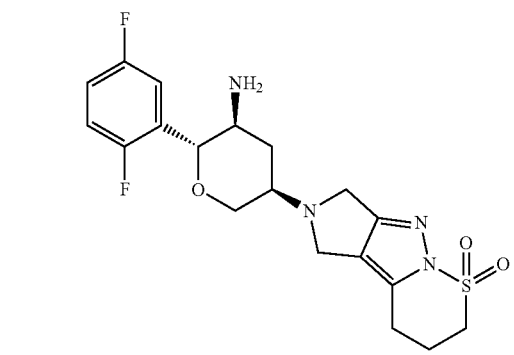

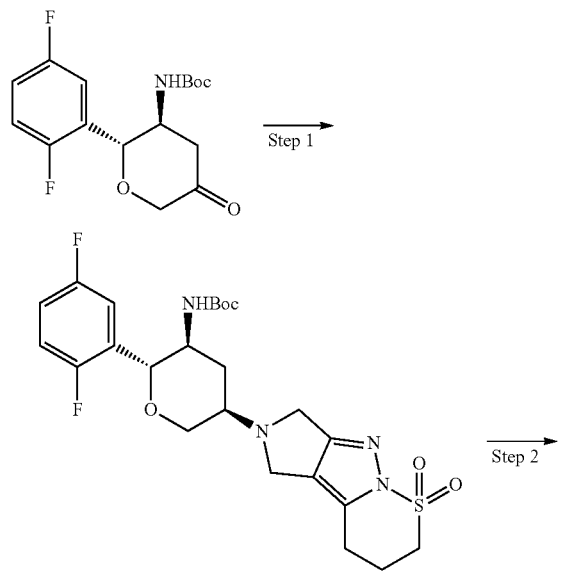

Step 1: tert-butyl (2R,3S,5R)-5-(2,3,4,5,6,7-hexahydropyrrolo[3',4':3,4]pyrazolo[1,5-b][1,2]thiazine-1,1-dioxide-6-yl)-2-(2,5-difluorophenyl)tetrahydro-2H-pyran-3-yl carbamate

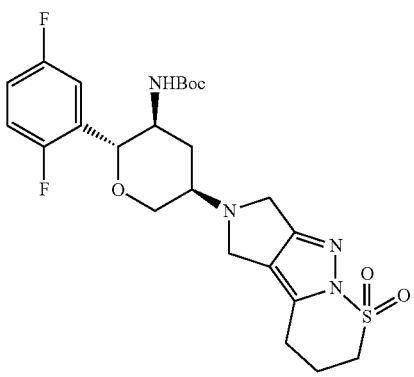 [SMILES: CC(C)(C)OC(=O)N[C@H]1C[C@@H](N2Cc3nn4c(c3C2)CCCS4(=O)=O)CO[C@@H]1c1cc(F)ccc1F]

To N,N-dimethylacetamide (2 mL) were added tert-butyl (2R,3S)-2-(2,5-difluorophenyl)-5-oxotetrahydro-2H-pyran-3-ylcarbamate (48 mg, 0.146 mmol), 2,3,4,5,6,7-hexahydropyrrolo [3',4':3,4]pyrazolo[1,5-b][1,2]thiazine-1,1-dioxide p-toluenesulfonate (48 mg, 0.13 mmol) and triethylamine (10 mg, 0.1 mmol), and stirred at room temperature for 3 hours. After cooling in an ice bath, sodium triacetoxyborohydride (87 mg, 0.39 mmol) was added, slowly warmed to room temperature and stirred overnight. Saturated sodium bicarbonate solution was added, and the resulting mixture was extracted with dichloromethane, washed with saturated brine, dried, concentrated and then purified by silica gel column chromatography to give tert-butyl (2R,3S,5R)-5-(2, 3,4,5,6,7-hexahydropyrrolo[3',4':3,4]pyrazolo[1,5-b][1,2] thiazine-1,1-dioxide-6-yl)-2-(2,5-difluorophenyl)tetrahydro-2H-pyran-3-ylcarbamate (48 mg). Yield: 71%. MS m/z[ESI]: 525.2[M+1]. $^1$H NMR (400 MHz, CDCl$_3$): δ=7.20 (1H, m), 6.98 (2H, m) 4.53 (1H, m), 4.16 (4H, m), 4.02 (2H, m), 3.64 (2H, m), 3.32 (3H, m), 2.80 (2H, m), 2.56 (2H, m), 2.39 (1H, m), 1.45 (1H, m), 1.26 (9H, s).

Step 2: (2R,3S,5R)-5-(2,3,4,5,6,7-hexahydropyrrolo [3',4':3,4]pyrazolo[1,5-b][1,2]thiazine-1,1-dioxide-6-yl)-2-(2,5-difluorophenyl)tetrahydro-2H-pyran-3-amine

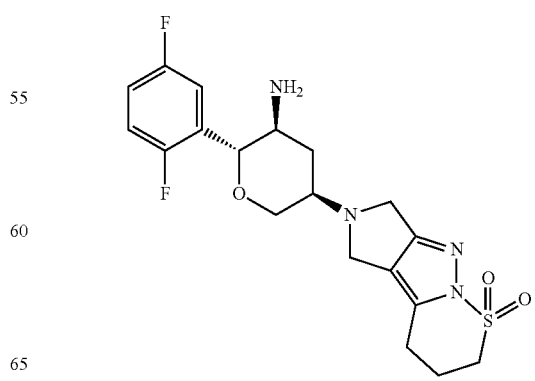

To dichloromethane (1 mL) were added tert-butyl 5-(2,3,4,5,6,7-hexahydropyrrolo[3',4':3, 4]pyrazolo[1,5-b][1,2]thiazine-1,1-dioxide-6-yl)-2-(2,5-difluorophenyl)tetrahydro-2H-pyran-3-yl carbamate (45 mg, 0.086 mmol), p-toluenesulfonic acid monohydrate (75 mg, 0.43 mmol), and stirred at room temperature overnight. Saturated sodium bicarbonate solution was added, and the resulting mixture was extracted with dichloromethane, spin-evaporated to dryness and then purified by silica gel column chromatography to give (2R,3S,5R)-5-(2,3,4,5,6,7-hexahydropyrrolo[3',4': 3,4]pyrazolo[1,5-b][1,2]thiazine-1,1-dioxide-6-yl)-2-(2,5-difluorophenyl)tetrahydro-2H-pyran-3-amine (15 mg). Yield 42%. MS m/z [ESI]: 425.1[M+1]. $^1$H NMR (400 MHz, CDCl$_3$): δ=7.14 (1H, m), 7.01 (2H, m), 4.18 (4H, m), 4.03 (2H, m), 3.66 (2H, m), 3.32 (3H, m), 2.80 (2H, m), 2.56 (2H, m), 2.35 (1H, m), 1.38 (1H, m), 1.26 (2H, brs).

Example 2: 5-((3R,5 S,6R)-5-amino-6-(2,5-difluorophenyl)tetrahydro-2H-pyran-3-yl)-3-methyl-1-methylsulfonyl-1,4,5,6-tetrahydropyrrolo[3,4-c]pyrazole

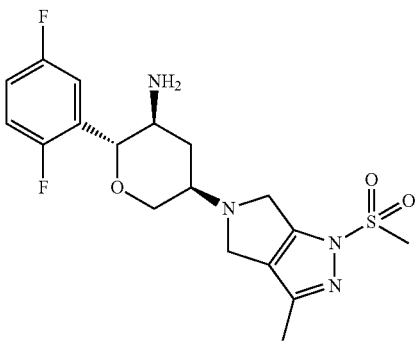 [SMILES: Cc1nn(S(C)(=O)=O)c2c1CN([C@H]1CO[C@H](c3cc(F)ccc3F)[C@@H](N)C1)C2]

Step 1: 5-((3R,5 S,6R)-5-tert-butoxycarbonylamino-6-(2,5-difluorophenyl)tetrahydro-2H-pyran-3-yl)-3-methyl-1,4,5,6-tetrahydropyrrolo[3,4-c]pyrazole

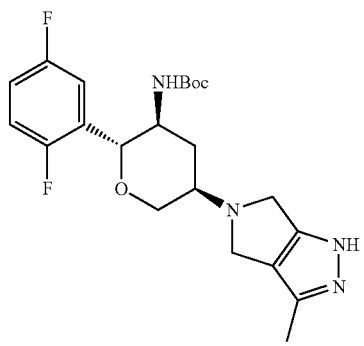 [SMILES: Cc1n[nH]c2c1CN([C@H]1CO[C@H](c3cc(F)ccc3F)[C@@H](NC(=O)OC(C)(C)C)C1)C2]

To 1,2-dichloroethane (10 mL) were added tert-butyl (2R,3S)-2-(2,5-difluorophenyl)-5-oxotetrahydro-2H-pyran-3-ylcarbamate (327 mg, 1 mmol), 3-methyl-2,4,5,6-tetrahydropyrrolo[3, 4-c]pyrazole (123 mg, 1 mmol) and glacial acetic acid (30 mg, 0.5 mmol), and stirred at room temperature for 2 hours. After cooling in an ice bath, sodium triacetoxyborohydride (672 mg, 3 mmol) was added, slowly warmed to room temperature and stirred overnight. Saturated sodium bicarbonate solution was added, and the resulting mixture was extracted with dichloromethane, washed with saturated brine, dried, concentrated and then purified by silica gel column chromatography to give 5-((3R,5 S,6R)-5-tert-butoxycarbonylamino-6-(2,5-difluorophenyl) tetrahydro-2H-pyran-3-yl)-3-methyl-1,4,5,6-tetrahydropyrrolo[3,4-c]pyrazole (145 mg). Yield: 33%. MS m/z[ESI]: 435.2 [M+1].

Step 2: 5-((3R,5 S,6R)-5-tert-butoxycarbonylamino-6-(2,5-difluorophenyl)tetrahydro-2H-pyran-3-yl)-3-methyl-1-methylsulfonyl-1,4,5,6-tetrahydropyrrolo[3,4-c]pyrazole

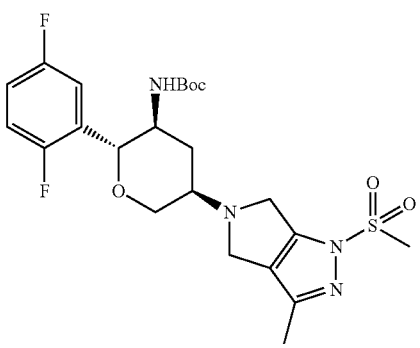 [SMILES: Cc1nn(S(C)(=O)=O)c2c1CN([C@H]1CO[C@H](c3cc(F)ccc3F)[C@@H](NC(=O)OC(C)(C)C)C1)C2]

To tetrahydrofuran (10 mL) were added 5-((3R,5S,6R)-5-tert-butoxycarbonylamino-6-(2,5-difluorophenyl)tetrahydro-2H-pyran-3-yl)-3-methyl-1,4,5,6-tetrahydropyrrolo[3,4-c]pyrazole (145 mg, 0.33 mmol) and triethylamine (53 mg, 0.53 mmol), and cooled in an ice bath. Methylsulfonyl chloride (49 mg, 0.43 mmol) was then added, and stirred for 2 hours. The reaction mixture was poured into water, and extracted with dichloromethane. The organic phase was dried, and the residue was purified by silica gel column chromatography to give 5-((3R,5 S,6R)-5-tert-butoxycarbonylamino-6-(2,5-difluorophenyl)tetrahydro-2H-pyran-3-yl)-3-methyl-1-methylsulfonyl-1,4,5,6-tetrahydropyrrolo[3, 4-c]pyrazole (16 mg). Yield: 9.5%. MS m/z[ESI]: 513.2[M+1]. H NMR (400 MHz, CDCl$_3$): δ=7.21 (1H, m), 6.96 (2H, m), 4.52 (1H, m), 4.37-4.20 (2H, m), 4.08 (2H, m), 3.75 (3H, m), 3.39 (1H, m), 3.28 (3H, s), 3.07 (1H, m), 2.48 (1H, m), 2.26 (3H, s), 1.53 (1H, m), 1.27 (9H, s).

Step 3: 5-((3R,5 S,6R)-5-amino-6-(2,5-difluorophenyl)tetrahydro-2H-pyran-3-yl)-3-methyl-1-methylsulfonyl-1,4,5,6-tetrahydropyrrolo[3,4-c]pyrazole

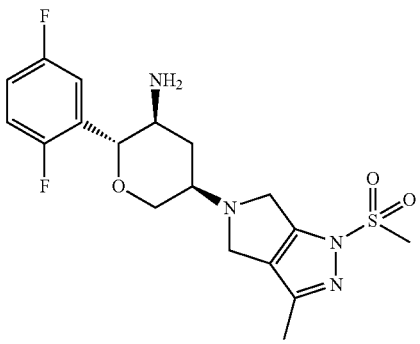 [SMILES: Cc1nn(S(C)(=O)=O)c2c1CN([C@H]1CO[C@H](c3cc(F)ccc3F)[C@@H](N)C1)C2]

To dichloromethane (0.7 mL) were added 5-((3R,5S,6R)-5-tert-butoxycarbonylamino-6-(2,5-difluorophenyl)tetrahydro-2H-pyran-3-yl)-3-methyl-1-methylsulfonyl-1,4,5,6-tetrahydropyrrolo[3,4-c]pyrazole (16 mg, 0.031 mmol), and benzenesulfonic acid (20 mg, 0.125 mmol), and stirred at room temperature overnight. Triethylamine (23 mg, 0.228 mmol) was added, and the solvent was removed by spin-evaporation, and then the residue was purified by silica gel column chromatography to give 5-((3R,5 S,6R)-5-amino-6-(2,5-difluorophenyl)tetrahydro-2H-pyran-3-yl)-3-methyl-1-methylsulfonyl-1,4,5,6-tetrahydropyrrolo[3,4-c]pyrazole (1.7 mg). Yield: 13%. MS m/z [ESI]: 413.2 [M+1]. $^1$H NMR (400 MHz, CDCl$_3$): δ=7.16 (1H, m), 7.01 (2H, m), 4.30 (1H, m), 4.22 (1H, m), 4.10 (1H, m), 3.90-3.70 (3H, m), 3.42 (1H, m), 3.27 (3H, s), 3.02 (2H, m), 2.48 (2H, m), 2.26 (3H, s), 2.00 (1H, m), 1.60 (1H, m).

Example 3: 5-((3R,5 S,6R)-5-amino-6-(2,5-difluorophenyl)tetrahydro-2H-pyran-3-yl)-5,6-dihydro-4H-thieno[3,2-c]pyrrole-2-carboxylic acid

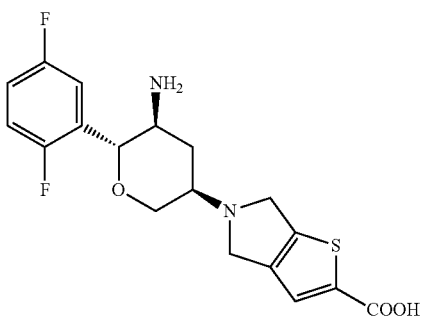 [SMILES: N[C@H]1C[C@@H](N2Cc3cc(C(=O)O)sc3C2)CO[C@@H]1c1cc(F)ccc1F]

Step 1: 5-((3R,5 S,6R-5-tert-butoxycarbonylamino-6-(2,5-difluorophenyl)tetrahydro-2H-pyran-3-yl)-5,6-dihydro-4H-thieno[3,2-c]pyrrole-2-carboxylic acid

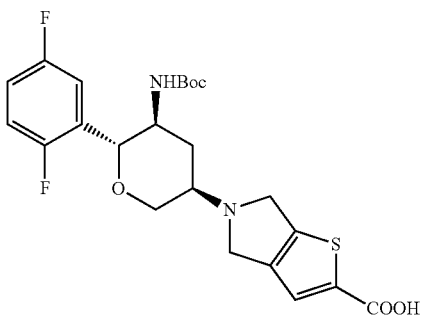 [SMILES: CC(C)(C)OC(=O)N[C@H]1C[C@@H](N2Cc3cc(C(=O)O)sc3C2)CO[C@@H]1c1cc(F)ccc1F]

The target compound was prepared according to the method of Step 1 in Example 1, except that 5,6-dihydro-4H-thieno[3,2-c]pyrrole-2-carboxylic acid hydrochloride (commercially available) was used instead of 2,3,4,5,6,7-hexahydropyrrolo[3',4':3,4]pyrazolo[1,5-b][1,2]thiazine-1,1-dioxide p-toluenesulfonate. Yield: 44%. MS m/z [ESI]: 481.1[M+1]. $^1$H NMR (400 MHz, CDCl$_3$): δ=9.22 (1H, s), 7.56 (1H, s), 7.11 (1H, m), 6.96 (2H, m), 4.55 (1H, m), 4.30 (2H, m), 4.12 (2H, m), 3.96 (2H, m), 3.80 (1H, m), 3.47 (1H, m), 3.05 (1H, m), 2.52 (1H, m), 1.58 (1H, m), 1.26 (9H, s).

Step 2: 5-((3R,5S,6R)-5-amino-6-(2,5-difluorophenyl)tetrahydro-2H-pyran-3-yl)-5,6-dihydro-4H-thieno[3,2-c]pyrrole-2-carboxylic acid

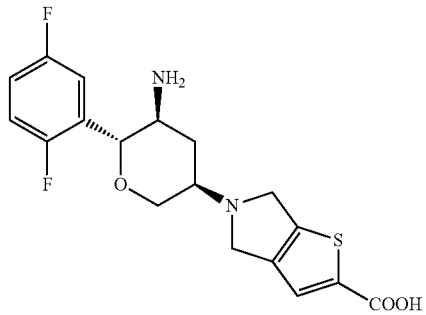 [SMILES: N[C@H]1C[C@@H](N2Cc3cc(C(=O)O)sc3C2)CO[C@@H]1c1cc(F)ccc1F]

The target compound was prepared according to the method of Step 2 in Example 1, except that 5-((3R,5S,6R)-5-tert-butoxycarbonylamino-6-(2,5-difluorophenyl) tetrahydro-2H-pyran-3-yl)-5, 6-dihydro-4H-thieno[3,2-c]pyrrole-2-carboxylic acid was used instead of tert-butyl 5-(2, 3,4,5,6,7-hexahydropyrrolo[3',4':3,4]pyrazolo[1,5-b][1,2]thiazine-1,1-dioxide-6-yl)-2-(2,5-difluorophenyl)tetrahydro-2H-pyran-3-ylcarbamate. Yield: 61%. MS m/z [ESI]: 381.1[M+1]. $^1$H NMR (400 MHz, DMSO-d$_6$): δ=7.35-7.10 (3H, m), 7.06 (1H, s), 4.12 (2H, m), 3.90 (2H, m), 3.76 (2H, m), 3.23 (1H, m), 2.82 (2H, m), 2.28 (1H, m), 1.37 (1H, m).

Example 4: (2R,3S,5R)-5-(5-methylsulfonylisoindolin-2-yl)-2-(2,5-difluorophenyl)tetrahydro-2H-pyran-3-amine

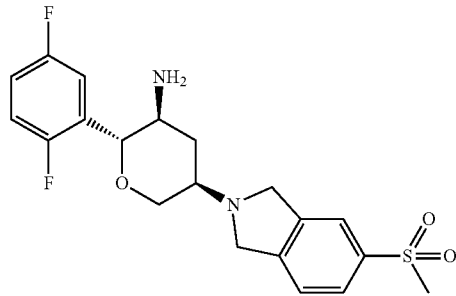 [SMILES: CS(=O)(=O)c1ccc2c(c1)CN([C@H]1CO[C@H](c3cc(F)ccc3F)[C@@H](N)C1)C2]

Step 1: tert-butyl (2R,3S,5R)-5-(5-methylsulfonylisoindolin-2-yl)-2-(2,5-difluorophenyl) tetrahydro-2H-pyran-3-ylcarbamate

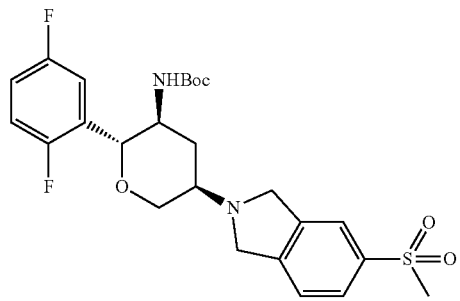 [SMILES: CC(C)(C)OC(=O)N[C@H]1C[C@@H](N2Cc3ccc(S(C)(=O)=O)cc3C2)CO[C@@H]1c1cc(F)ccc1F]

The target compound was prepared according to the method of Step 1 in Example 1, except that 5-methylsulfonylisoindoline hydrochloride was used instead of 2,3,4,5,6,7-hexahydropyrrolo [3',4':3,4]pyrazolo[1,5-b][1,2]thiazine-1,1-dioxide p-toluenesulfonate. Yield: 54%. MS m/z[ESI]: 509.2[M+1]. ¹H NMR (400 MHz, CDCl₃): δ=7.83 (1H, d, J=8.0 Hz), 7.82 (1H, s), 7.42 (1H, d, J=8.0 Hz), 7.24 (1H, m), 6.97 (2H, m), 4.50 (1H, m), 4.32 (2H, m), 4.08 (4H, m), 3.80 (1H, m), 3.43 (1H, t, J=10.6 Hz), 3.04 (3H, s), 2.95 (1H, m), 2.54 (1H, m), 1.54 (1H, m), 1.28 (9H, s).

Step 2: (2R,3S,5R)-5-(5-methylsulfonylisoindolin-2-yl)-2-(2,5-difluorophenyl)tetrahydro-2H-pyran-3-amine

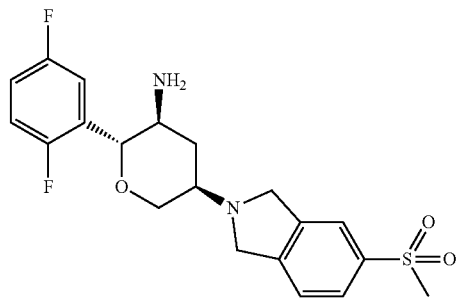 [SMILES: CS(=O)(=O)c1ccc2c(c1)CN([C@H]1CO[C@H](c3cc(F)ccc3F)[C@@H](N)C1)C2]

The target compound was prepared according to the method of Step 2 in Example 1, except that tert-butyl (2R,3S,5R)-5-(5-methylsulfonylisoindolin-2-yl)-2-(2,5-difluorophenyl)tetrahydro-2H-pyran-3-ylcarbamate was used instead of tert-butyl 5-(2,3,4,5,6,7-hexahydropyrrolo[3',4':3,4] pyrazolo[1,5-b][1,2]thiazine-1,1-dioxide-6-yl)-2-(2,5-difluorophenyl)tetrahydro-2H-pyran-3-ylcarbamate. Yield: 68%. MS m/z [ESI]: 409.1[M+1]. ¹H NMR (400 MHz, CDCl₃): δ=7.83 (1H, d, J=8.0 Hz), 7.82 (1H, s), 7.42 (1H, d, J=8.0 Hz), 7.17 (1H, m), 7.02 (2H, m), 4.28 (1H, m), 4.24 (2H, d, J=9.6 Hz), 4.09 (4H, m), 3.45 (1H, m), 3.04 (3H, s), 2.92 (2H, m), 2.49 (1H, m), 1.47 (1H, m), 1.30 (2H, brs).

Example 5: (2R,3S,5R)-5-(5-methylsulfonamido-isoindolin-2-yl)-2-(2,5-difluorophenyl) tetrahydro-2H-pyran-3-amine

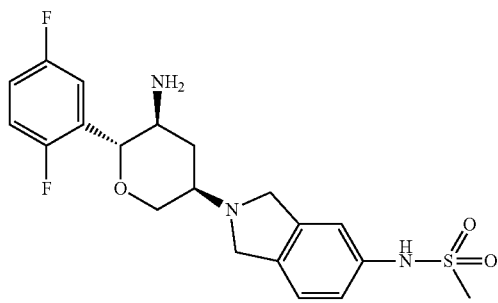 [SMILES: CS(=O)(=O)Nc1ccc2c(c1)CN([C@H]1CO[C@H](c3cc(F)ccc3F)[C@@H](N)C1)C2]

Step 1: tert-butyl (2R,3S,5R)-5-(5-methylsulfonamidoisoindolin-2-yl)-2-(2,5-difluorophenyl) tetrahydro-2H-pyran-3-ylcarbamate

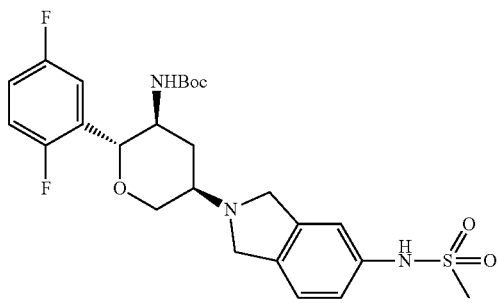 [SMILES: CC(C)(C)OC(=O)N[C@H]1C[C@@H](N2Cc3ccc(NS(C)(=O)=O)cc3C2)CO[C@@H]1c1cc(F)ccc1F]

According to the method of Step 1 in Example 1, 5-methylsulfonamidoisoindoline was used instead of 2,3,4,5,6,7-hexahydropyrrolo[3',4':3,4]pyrazolo[1,5-b][1,2]thiazine-1,1-dioxide p-toluenesulfonate. Yield: 50%. MS m/z[ESI]: 524.2[M+1].

Step 2: (2R,3S,5R)-5-(5-methylsulfonamidoisoindolin-2-yl)-2-(2,5-difluorophenyl) tetrahydro-2H-pyran-3-amine

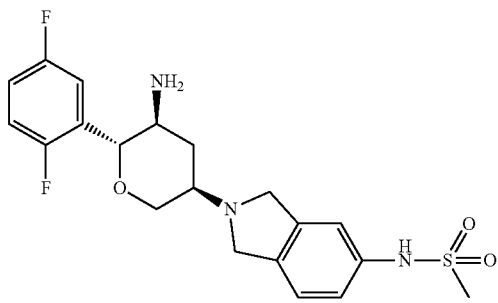

The target compound was prepared according to the method of Step 2 in Example 1, except that tert-butyl (2R,3S,5R)-5-(5-methylsulfonamidoisoindolin-2-yl)-2-(2,5-difluorophenyl) tetrahydro-2H-pyran-3-yl carbamate was used instead of tert-butyl 5-(2,3,4,5,6,7-hexahydropyrrolo [3',4':3,4]pyrazolo[1,5-b][1,2]thiazine-1,1-dioxide-6-yl)-2-(2,5-difluorophenyl)-tetrahydro-2H-pyran-3-ylcarbamate. Yield: 57%. MS m/z [ESI]: 424.1[M+1]. ¹H NMR (400 MHz, CDCl₃): δ=7.24 (1H, m), 7.17 (1H, m), 7.07-6.90 (4H, m), 5.35 (1H, s), 4.35-4.20 (2H, m), 4.08 (4H, m), 3.65 (2H, m), 3.00 (3H, s), 2.82 (1H, m), 2.32 (1H, m), 1.47 (1H, m), 1.25 (2H, brs).

Example 6: (2R,3S,5R)-5-(5-bromoisoindolin-2-yl)-2-(2,5-difluorophenyl)tetrahydro-2H-pyran-3-amine

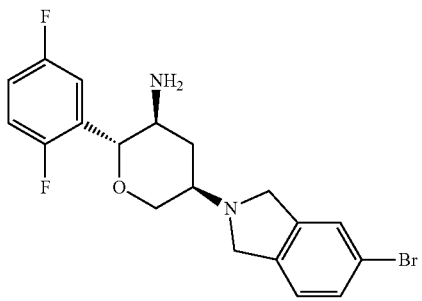 [SMILES: N[C@H]1C[C@@H](N2Cc3ccc(Br)cc3C2)CO[C@@H]1c1cc(F)ccc1F]

Step 1: tert-butyl (2R,3S,5R)-5-(5-bromoisoindolin-2-yl)-2-(2,5-difluorophenyl)tetrahydro-2H-pyran-3-ylcarbamate

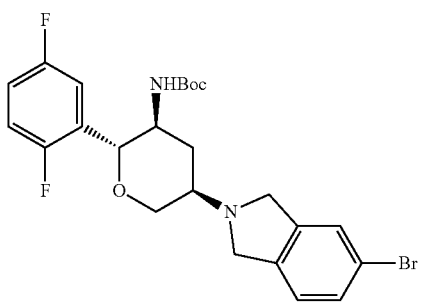 [SMILES: CC(C)(C)OC(=O)N[C@H]1C[C@@H](N2Cc3ccc(Br)cc3C2)CO[C@@H]1c1cc(F)ccc1F]

The target compound was prepared according to the method of Step 1 in Example 1, except that 5-bromoisoindoline was used instead of 2,3,4,5,6,7-hexahydropyrrolo[3',4':3,4]pyrazolo[1,5-b][1,2]thiazine-1,1-dioxide p-toluenesulfonate. Yield: 62%. MS m/z [ESI]: 509.1[M+1]. $^1$H NMR (400 MHz, CDCl$_3$): δ=7.36 (1H, s), 7.34 (1H, d, J=8.0 Hz), 7.23 (1H, m), 7.09 (1H, d, J=8.0 Hz), 6.97 (2H, m), 4.49 (1H, m), 4.30 (2H, m), 3.94 (4H, m), 3.79 (1H, m), 3.42 (1H, t, J=10.8 Hz), 2.92 (1H, m), 2.52 (1H, d, J=10.8 Hz), 1.54 (1H, m), 1.27 (9H, s).

Step 2: (2R,3S,5R)-5-(5-bromoisoindolin-2-yl)-2-(2,5-difluorophenyl)tetrahydro-2H-pyran-3-amine

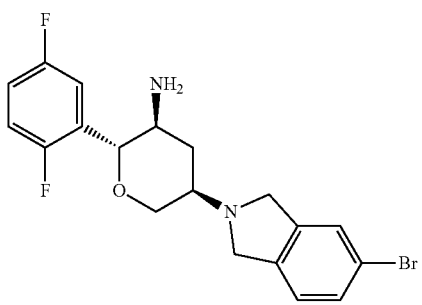 [SMILES: N[C@H]1C[C@@H](N2Cc3ccc(Br)cc3C2)CO[C@@H]1c1cc(F)ccc1F]

The target compound was prepared according to the method of Step 2 in Example 1, except that tert-butyl (2R,3S,5R)-5-(5-bromoisoindolin-2-yl)-2-(2,5-difluorophenyl)tetrahydro-2H-pyran-3-ylcarbamate was used instead of tert-butyl 5-(2,3,4,5,6,7-hexahydropyrrolo[3',4':3,4]pyrazolo [1,5-b][1,2]thiazine-1,1-dioxide-6-yl)-2-(2,5-difluorophenyl)tetrahydro-2H-pyran-3-ylcarbamate. Yield: 69%. MS m/z [ESI]: 409.1[M+1]. $^1$H NMR (400 MHz, CDCl$_3$): δ=7.37 (1H, s), 7.34 (1H, d, J=8.0 Hz), 7.15 (1H, m), 7.10 (1H, d, J=8.0 Hz), 7.02 (2H, m), 4.27 (1H, m), 4.22 (1H, d, J=9.2 Hz), 3.99 (4H, m), 3.79 (1H, m), 3.42 (1H, t, J=10.8 Hz), 2.87 (2H, m), 2.47 (1H, d, J=10.8 Hz), 1.48 (1H, m), 1.32 (2H, brs).

Example 7: (2R,3S,5R)-5-(4-chloro-5-methylsulfonylisoindolin-2-yl)-2-(2,5-difluorophenyl) tetrahydro-2H-pyran-3-amine

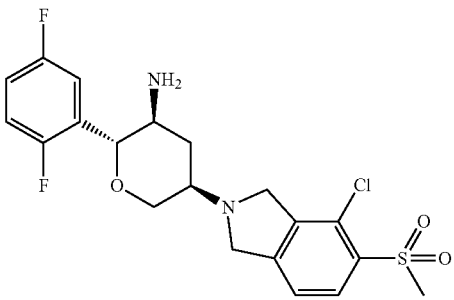 [SMILES: CS(=O)(=O)c1ccc2c(c1Cl)CN([C@H]1CO[C@H](c3cc(F)ccc3F)[C@@H](N)C1)C2]

Step 1: tert-butyl (2R,3S,5R)-5-(4-chloro-5-methylsulfonylisoindolin-2-yl)-2-(2,5-difluorophenyl)tetrahydro-2H-pyran-3-ylcarbamate

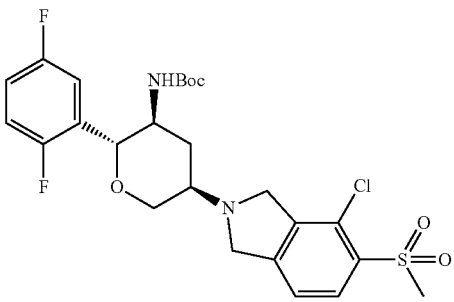 [SMILES: CC(C)(C)OC(=O)N[C@H]1C[C@@H](N2Cc3ccc(S(C)(=O)=O)c(Cl)c3C2)CO[C@@H]1c1cc(F)ccc1F]

The target compound was prepared according to the method of Step 1 in Example 1, except that 4-chloro-5-methylsulfonylisoindoline was used instead of 2,3,4,5,6,7-hexahydropyrrolo[3',4':3,4]pyrazolo[1,5-b][1,2]thiazine-1,1-dioxide p-toluenesulfonate. Yield: 56%. MS m/z [ESI]: 543.1[M+1].

Step 2: (2R,3S,5R)-5-(4-chloro-5-methylsulfonylisoindolin-2-yl)-2-(2,5-difluorophenyl) tetrahydro-2H-pyran-3-amine

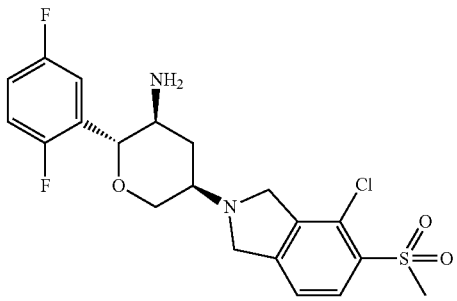 [SMILES: CS(=O)(=O)c1ccc2c(c1Cl)CN([C@H]1CO[C@H](c3cc(F)ccc3F)[C@@H](N)C1)C2]

The target compound was prepared according to the method of Step 2 in Example 1, except that tert-butyl (2R,3S,5R)-5-(4-chloro-5-methylsulfonylisoindolin-2-yl)-2-(2,5-difluorophenyl) tetrahydro-2H-pyran-3-yl carbamate was used instead of tert-butyl 5-(2,3,4,5,6,7-hexahydropyrrolo[3',4':3,4]pyrazolo[1,5-b][1,2]thiazine-1,1-dioxide-6-yl)-2-(2,5-difluorophenyl) tetrahydro-2H-pyran-3-ylcarbamate. Yield: 47%. MS m/z [ESI]: 443.1[M+1]. ¹H NMR (400 MHz, CDCl₃): δ=8.06 (1H, d, J=7.6 Hz), 7.33 (1H, d, J=7.6 Hz), 7.19 (1H, m), 6.99 (2H, m), 4.69 (1H, m), 4.22 (4H, m), 3.71 (1H, m), 3.33 (1H, m), 3.27 (3H, s), 2.91 (1H, m), 2.61 (2H, m), 1.52 (1H, m), 1.32 (2H, brs).

Example 8: 2-((3R,5 S,6R)-5-amino-6-(2,5-difluorophenyl)tetrahydro-2H-pyran-3-yl) isoindoline-5-sulfonamide

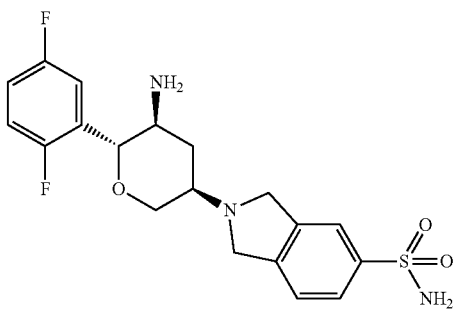 [SMILES: N[C@H]1C[C@@H](N2Cc3ccc(S(N)(=O)=O)cc3C2)CO[C@@H]1c1cc(F)ccc1F]

Step 1: 2-((3R,5 S,6R)-5-tert-butoxycarbonylamino-6-(2,5-difluorophenyl)tetrahydro-2H-pyran-3-yl) isoindoline-5-sulfonamide

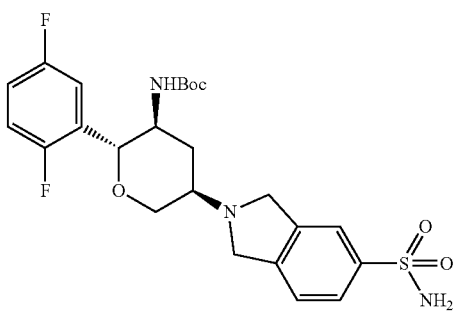 [SMILES: CC(C)(C)OC(=O)N[C@H]1C[C@@H](N2Cc3ccc(S(N)(=O)=O)cc3C2)CO[C@@H]1c1cc(F)ccc1F]

The target compound was prepared according to the method of Step 1 in Example 1, except that isoindoline-5-sulfonamide hydrochloride was used instead of 2,3,4,5,6,7-hexahydropyrrolo[3',4':3,4]pyrazolo[1,5-b][1,2]thiazine-1,1-dioxide p-toluenesulfonate. Yield: 46%. MS m/z[ESI]: 510.2[M+1].

Step 2: 2-((3R,5S,6R)-5-amino-6-(2,5-difluorophenyl)tetrahydro-2H-pyran-3-yl) isoindoline-5-sulfonamide

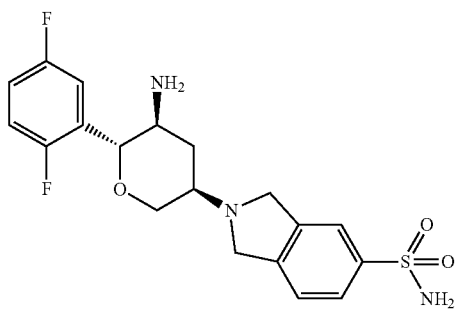 [SMILES: N[C@H]1C[C@@H](N2Cc3ccc(S(N)(=O)=O)cc3C2)CO[C@@H]1c1cc(F)ccc1F]

The target compound was prepared according to the method of Step 2 in Example 1, except that 2-((3R,5 S,6R)-5-tert-butoxycarbonylamino-6-(2,5-difluorophenyl) tetrahydro-2H-pyran-3-yl) isoindoline-5-sulfonamide was used instead of tert-butyl 5-(2,3,4,5,6,7-hexahydropyrrolo[3',4':3,4]pyrazolo[1,5-b][1,2]thiazine-1,1-dioxide-6-yl)-2-(2,5-difluorophenyl)tetrahydro-2H-pyran-3-yl carbamate. Yield: 37%. MS m/z [ESI]: 410.1[M+1]. ¹H NMR (400 MHz, CDCl₃): δ=7.81 (1H, d, J=7.6 Hz), 7.80 (1H, s), 7.37 (1H, d, J=7.6 Hz), 7.17 (1H, m), 7.02 (2H, m), 4.79 (2H, brs), 4.28 (1H, d, J=9.6 Hz), 4.23 (1H, d, J=9.6 Hz), 4.07 (4H, m), 3.43 (1H, t, J=10.8 Hz), 2.90 (2H, m), 2.49 (1H, m), 1.49 (1H, m), 1.31 (2H, brs).

Example 9: (2R,3S,5R)-5-(5-cyclopropyl sulfonylisoindolin-2-yl)-2-(2,5-difluorophenyl) tetrahydro-2H-pyran-3-amine

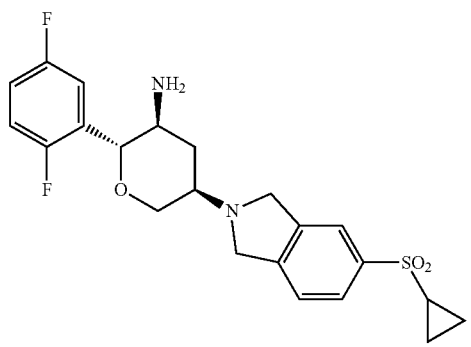 [SMILES: N[C@H]1C[C@@H](N2Cc3ccc(S(=O)(=O)C4CC4)cc3C2)CO[C@@H]1c1cc(F)ccc1F]

Step 1: tert-butyl (2R,3S,5R)-5-(5-cyclopropyl sulfonylisoindolin-2-yl)-2-(2,5-difluorophenyl) tetrahydro-2H-pyran-3-ylcarbamate

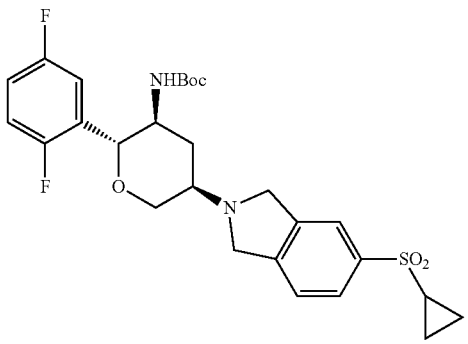 [SMILES: CC(C)(C)OC(=O)N[C@H]1C[C@@H](N2Cc3ccc(S(=O)(=O)C4CC4)cc3C2)CO[C@@H]1c1cc(F)ccc1F]

The target compound was prepared according to the method of Step 1 in Example 1, except that 5-cyclopropylsulfonylisoindoline hydrochloride was used instead of 2,3,4,5,6,7-hexahydropyrrolo [3',4':3,4]pyrazolo[1,5-b][1,2]thiazine-1,1-dioxide p-toluenesulfonate. Yield: 53%. MS m/z [ESI]: 535.2[M+1].

Step 2: (2R,3S,5R)-5-(5-cyclopropylsulfonylisoindolin-2-yl)-2-(2,5-difluorophenyl)tetrahydro-2H-pyran-3-amine

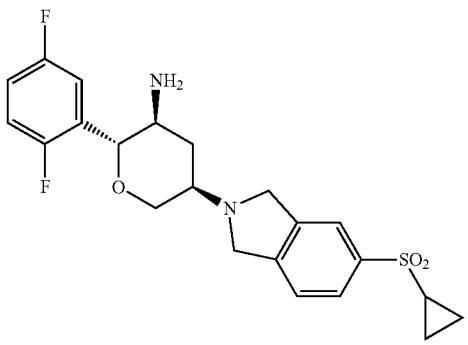 [SMILES: N[C@H]1C[C@@H](N2Cc3ccc(S(=O)(=O)C4CC4)cc3C2)CO[C@@H]1c1cc(F)ccc1F]

The target compound was prepared according to the method of Step 2 in Example 1, except that tert-butyl (2R,3S,5R)-5-((5-cyclopropylsulfonylisoindolin-2-yl)-2-(2,5-difluorophenyl) tetrahydro-2H-pyran-3-yl carbamate was used instead of tert-butyl 5-(2,3,4,5,6,7-hexahydropyrrolo[3',4':3,4]pyrazolo[1,5-b][1,2]thiazine-1,1-dioxide-6-yl)-2-(2,5-difluorophenyl) tetrahydro-2H-pyran-3-ylcarbamate. Yield: 80%. MS m/z [ESI]: 435.2[M+1]. $^1$H NMR (400 MHz, CDCl$_3$): δ=7.77 (1H, d, J=8.0 Hz), 7.76 (1H, s), 7.42 (1H, d, J=8.0 Hz), 7.17 (1H, m), 7.02 (2H, m), 4.30 (2H, m), 4.10 (4H, m), 3.54 (1H, t, J=10.8 Hz), 3.24 (1H, m), 2.95 (2H, m), 2.45 (1H, m), 1.52 (1H, m), 1.28 (2H, brs), 1.05 (2H, m), 0.87 (2H, m).

Biological Experimental Example 1: Measuring DPP-IV Inhibitory Activity

DPP-IV inhibitory activity in plasma of compounds of the present application was determined by using the following method, which was expressed as IC$_{50}$ values, i.e., the concentrations of the compounds required to achieve 50% inhibition of DPP-IV activity.

Materials and Methods:
Materials:
a. White 384-well plate (Perkin Elmer, Catalog No. 607290/99)
b. HEPES buffer: using 1M HEPES buffer (Invitrogen, Catalog No. 15630-080) to prepare 50 mL of 0.5M HEPES buffer by following the steps of taking 25 mL of 1 M HEPES buffer, adding an appropriate amount of ddH$_2$O (re-distilled water), adjusting the pH to 7.8 with NaOH, and finally adding ddH$_2$O to 50 mL.
c. Rat plasma: taking blood samples from rat orbit, adding heparin for anticoagulation, centrifuging at 4000 rpm for 10 minutes, taking supernatant plasma as an enzyme source of DPP-IV
d. H-Gly-Pro-AMC (glycine-proline-7-amino-4-methylcoumarin) as the enzyme reaction substrate of DPP-IV, which was synthesized by the inventors of the present application, was dissolved in DMSO to form 100 mM mother solution.
e. 1M MgCl$_2$
f. 1.5 MNaCl
g. 10% BAS
h. DMSO
i. ddH$_2$O
j. Test compounds: Omarigliptin as a positive control compound and parts of compounds in Examples of the present application.

Following the sequence below:
1. DPP-IV enzyme reaction buffer was prepared (50 mM HEPES (pH=7.8), 80 mM MgCl$_2$, 150 mM NaCl, 1% BSA), and stored on ice for use;
2. The test compounds were diluted with DMSO from 10 mM to 1 mM (100-fold final concentration), and then diluted gradiently 3 folds in a 96-well plate to obtain 11 concentrations; DMSO was added to the twelfth well as a blank control, and then diluted 25 folds with the enzyme reaction buffer to 4-fold final concentration for use;
3. The DPP-IV enzyme reaction substrate H-Gly-Pro-AMC was thawed and diluted to 160 µM (4-fold final concentration) with the enzyme reaction buffer, and then stored on ice for use;
4. The rat plasma was thawed and diluted 100 folds (2-fold final concentration) with the enzyme reaction buffer, and then stored on ice for use;
5. 5 µL of the test compounds (4-fold final concentration) were added to a 384-well plate, and then L of the rat plasma (2-fold final concentration) was added, centrifuged and mixed well;
6. 5 µL of the enzyme reaction substrate H-Gly-Pro-AMC (4-fold final concentration) was added, centrifuged and mixed well, and then the 384-well plate was sealed with a film;
7. The resulting mixture was incubated in an incubator (22-23° C.) for 1 hour;
8. The fluorescence signal was determined using FlexStation3 (Molecular devices) microplate reader (excited at 380 nm, and the emission spectrum was determined at 460 nm wavelength);
9. IC$_{50}$ values of the test compounds in inhibiting DPP-IV activity were determined, i.e., calculating the IC$_{50}$ values of the compounds using GraFit6 software.

TABLE 1

DPP-IV inhibitory activity of the compounds of Examples

| Compound | Structure | IC$_{50}$ (nM) |
|---|---|---|
| Omarigliptin | 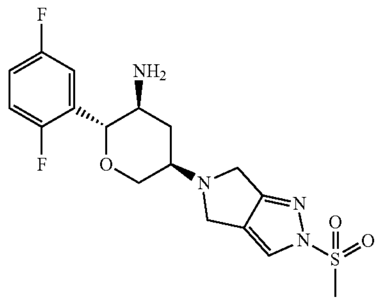 [SMILES: CS(=O)(=O)n1cc2c(n1)CN([C@H]1CO[C@H](c3cc(F)ccc3F)[C@@H](N)C1)C2] | 4.2 |
| Example 1 | 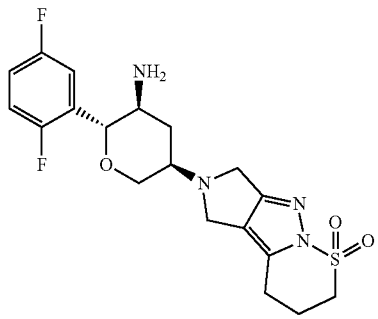 [SMILES: N[C@H]1C[C@@H](N2Cc3nn4c(c3C2)CCCS4(=O)=O)CO[C@@H]1c1cc(F)ccc1F] | 4.4 |
| Example 2 | 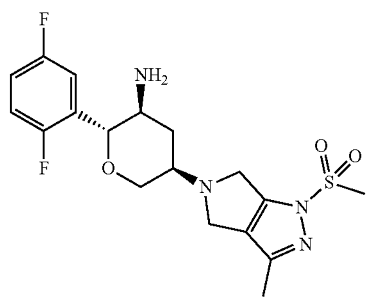 [SMILES: Cc1nn(S(C)(=O)=O)c2c1CN([C@H]1CO[C@H](c3cc(F)ccc3F)[C@@H](N)C1)C2] | 5.1 |
| Example 3 | 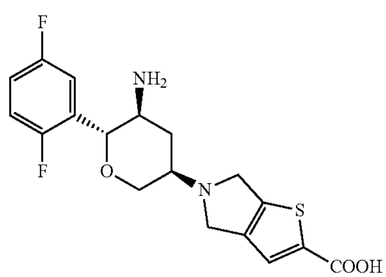 [SMILES: N[C@H]1C[C@@H](N2Cc3cc(C(=O)O)sc3C2)CO[C@@H]1c1cc(F)ccc1F] | 18.2 |
| Example 4 | 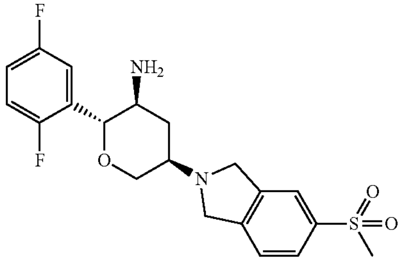 [SMILES: CS(=O)(=O)c1ccc2c(c1)CN([C@H]1CO[C@H](c3cc(F)ccc3F)[C@@H](N)C1)C2] | 2.6 |

TABLE 1-continued

DPP-IV inhibitory activity of the compounds of Examples

| Compound | Structure | IC$_{50}$ (nM) |
|---|---|---|
| Example 6 | 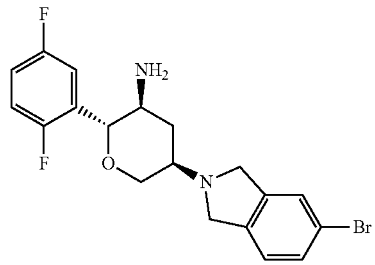 [SMILES: N[C@H]1C[C@@H](N2Cc3ccc(Br)cc3C2)CO[C@@H]1c1cc(F)ccc1F] | 6.5 |
| Example 8 | 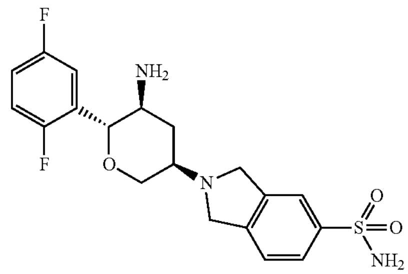 [SMILES: N[C@H]1C[C@@H](N2Cc3ccc(S(N)(=O)=O)cc3C2)CO[C@@H]1c1cc(F)ccc1F] | 3.8 |
| Example 9 | 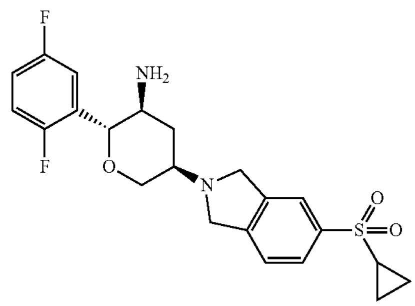 [SMILES: N[C@H]1C[C@@H](N2Cc3ccc(S(=O)(=O)C4CC4)cc3C2)CO[C@@H]1c1cc(F)ccc1F] | 3.2 |

Biological Experimental Example 2: Measuring Pharmacokinetics Parameters

The pharmacokinetic parameters of compounds of the present application were determined by using the following method.

Healthy male adult rats (7-9 weeks old) were used in this study. Each group of animals (3 male rats) was intragastrically administered once at a single dose of 5 mg/kg. The animals in the intragastric administration group were fasted overnight before this study. The fasting time period was from 10 hours before administration to 4 hours after administration.

Blood samples were taken at 0.25, 0.5, 1, 2, 4, 6, 8 and 24 h after administration. The animals were anesthetized with isoflurane using an animal anesthesia machine, and then 0.3 mL whole blood samples were taken from the fundus venous plexus. The blood samples were placed in heparin anticoagulant tubes, and centrifuged for 5 min at 4° C. and 4000 rpm. The resulting plasmas were transferred to centrifuge tubes, and stored at −80° C. until analysis.

Verified LC-MS/MS method was used to analyze the plasma samples. Plasma concentration-time data of animals were analyzed using WinNonlin (Professional Edition, version 6.3; Pharsight Company) software. The non-compartmental model was introduced for concentration analysis. The pharmacokinetic parameters of the compounds were calculated, and shown in Table 2 below.

TABLE 2

| | | PK value (20% sulfobutyl-β-cyclodextrin, PO, 5 mg/kg) | |
|---|---|---|---|
| Parameter | Unit | Compound of Example 4 | Compound of Example 9 |
| $T_{1/2}$ | hr | 17.1 | 32.5 |
| $T_{max}$ | hr | 1.67 | 2.00 |
| $C_{max}$ | ng/mL | 4387 | 5960 |
| $AUC_{0\text{-}inf}$ | hr · ng/mL | 45588 | 52179 |

Biological Experimental Example 3: Measuring $IC_{50}$ Value of Inhibiting CYP Enzyme System $IC_{50}$ values of compounds of the present application in inhibiting CYP enzyme system were determined by using the following method.

Human liver microsomes frozen at −80° C. in refrigerator were placed on ice for thawing, of which 100 μL was placed in a constant temperature oscillator for incubation (1 hour) at 60° C. and 100 rpm when immediately thawing, and the rest was frozen immediately in refrigerator at −80° C. After one hour, 100 μL inactivated liver microsomes were taken out, and thereto was added 400 μL phosphate buffer, and uniformly mixed to form a 4 mg/mL solution of inactivated liver microsomes. Meanwhile, human liver microsomes frozen at −80° C. in refrigerator were placed on ice for thawing, of which 100 μL was taken out when immediately thawing, and thereto was added 400 μL phosphate buffer, and uniformly mixed to form a 4 mg/mL solution of liver microsomes. The incubation mixtures for a positive control, test compounds and a negative control were prepared according to Table 3 below:

TABLE 3

Incubation mixtures for a positive control, test compounds and a negative control

| | Positive Control and Test Compounds | | | Negative Control Inactivated | | |
|---|---|---|---|---|---|---|
| CYP450 Enzyme | Liver Microsoms Solution (μL) | Substrate Solution (μL) | Phosphate Buffer (μL) | Liver Microsomes Solution (μL) | Substrate Solution (μL) | Phosphate Buffer (μL) |
| CYP1A2 | 13.0 | 88.0 | 3109.0 | 6.5 | 44.0 | 1554.5 |
| CYP2B6 | 7.0 | 88.0 | 3115.0 | 3.5 | 44.0 | 1557.5 |
| CYP2C8 | 30.0 | 88.0 | 3126.0 | 15.0 | 44.0 | 1563.0 |
| CYP2C9 | 35.0 | 88.0 | 3121.0 | 17.5 | 44.0 | 1560.5 |
| CYP2C19 | 175 | 88.0 | 2960.0 | 87.5 | 44.0 | 1480.0 |
| CYP2D6 | 13.0 | 116.0 | 3073.0 | 6.5 | 58.0 | 1536.5 |
| CYP3A4 Midazolam | 20.0 | 88.0 | 3078.0 | 10.0 | 44.0 | 1539.0 |
| CYP3A4 Testosterone | 23.0 | 90.0 | 3151.6 | 11.5 | 45.0 | 1575.8 |

The above incubation mixtures were incubated for 5 minutes in a constant temperature oscillator at 37° C. and 100 rpm.

To 2.5 μL working solution of the test compounds or positive control (the negative control was added to the working solution of the test compounds) were added 91.5 μL the incubation mixtures and 6 μL NADPH solution, and then the reaction was initiated via vortex. The resulting solutions were incubated in a constant temperature oscillator at 37° C. and 100 rpm, and the incubation time was shown in Table 4 below:

TABLE 4

| | Incubation Time | | | | | | | |
|---|---|---|---|---|---|---|---|---|
| CYP450 Enzyme | CYP1A2 | CYP2B6 | CYP2C8 | CYP2C9 | CYP2C19 | CYP2D6 | CYP3A4 Midazolam | CYP3A4 Testosterone |
| Time (min) | 30 | 20 | 15 | 15 | 30 | 30 | 10 | 20 |

After incubation, 200 µL of an internal standard solution (the internal standard solution of CYP2C19 was a 100 ng/mL solution of chloramphenicol in acetonitrile, and other internal standard solutions were a 250 ng/mL solution of warfarin in acetonitrile and 500 ng/mL solution of propranolol in acetonitrile) was added to terminate the reaction. Samples from the terminated reaction were centrifuged at 12000 rpm for 10 minutes, and supernatants were taken out for analysis.

Analyst 1.4.2 or equivalent software was used for data processing. Integrals were detected to ensure that all peaks were properly integrated, and if necessary, adjust integral parameters.

The quantification of an analyte was defined as a ratio of a peak area of the analyte to that of the internal standard. LC-MS/MS method was used for analysis. Parameters, such as $IC_{50}$ and the like, were calculated using the Graphpad Prism (Version 5.03) software. The results were shown in Table 5 below:

TABLE 5

$IC_{50}$ (µM) of Compound of Example 4 in inhibiting CYP Enzyme System

| | CYP Enzyme System | | | | | | | |
|---|---|---|---|---|---|---|---|---|
| | 1A2 | 2B6 | 2C8 | 2C9 | 2C19 | 2D6 | 3A4_Mid | 3A4_Tes |
| Positive Control | α-Naphthoflavone | Ticlopidine | Quercetin | Sulfaphenazole | Ticlopidine | Quinidine | Ketoconazole | Ketoconazole |
| Compound of Example 4 | >25 | >25 | >25 | >25 | >25 | >25 | >25 | >25 |
| Positive Control | 0.025 | 0.10 | 1.13 | 0.44 | 1.71 | 0.11 | 0.054 | 0.033 |

Biological Experimental Example 4: Liver Microsome Metabolic Stability

The liver microsome metabolic stability of compounds of the present application was determined by using the following method.

8 µL human liver microsomes (20 mg/mL), 20 µL NADPH and 368 µL of 0.1 M phosphate buffer were mixed, and then pre-incubated at 37° C. for 5 minutes. 4 µL working solutions (test compounds or positive control) were added, respectively. When pre-incubated at 37° C., 50 µL incubation solutions were taken out at 0, 10, 20, 30, 45 and 60 minute, and thereto was added a 150 µL solution of internal standard (0.25M warfarin) in acetonitrile. 4 µL rat liver microsomes (20 mg/mL), 10 µL NADPH and 184 µL of 0.1 M phosphate buffer were mixed, and then pre-incubated at 37° C. for 5 minutes. 2 µL working solutions (test compounds or positive control) were added, respectively. When pre-incubated at 37° C., 20 µL incubation solutions were taken out at 0, 10, 20, 30, 45 and 60 minute, and thereto was added a 180 µL solution of internal standard (0.25 M warfarin) in acetonitrile. All samples were vortexed and centrifuged at 4000 rpm for 15 min, and 150 µL supernatants were added to a 96-well plate, and then 5 µL supernatants were detected in LC/MS/MS system. Chromatographic column for analysis was C18 1.7 µm 2.1×50 mm (Waters). Triple quadrupole mass spectrometry (API4000, AB Company) was used in detection. A ratio of the peak area of CT-1225 to that of the internal standard was detected in positive ion mode. A half-life was represented as a ratio of the peak area of test compounds/internal standard to time. The results were shown in Table 6 below:

TABLE 6

Liver microsome metabolic stability of compound of Example 4 and reference compound

| | Half Life $t_{1/2}$ (hour) | |
|---|---|---|
| Compound | Rat | Human |
| Compound of Example 4 | 8.26 | 4.52 |
| Omarigliptin | 21.1 | 4.09 |

Biological Experimental Example 5: Inhibitory Effect of a Single Dose on Serum DPP-IV Activity in Ob/Ob Mice 36 female ob/ob mice were randomly divided into 6 groups (6 mice in each group), which are model control group, 1 mg/kg compound of Example 4 group, 3 mg/kg compound of Example 4 group, 10 mg/kg compound of Example 4 group, 30 mg/kg compound of Example 4 group and 30 mg/kg Omarigliptin (as positive control) group. The mice were orally administered with the compound of Example 4 or Omarigliptin at various doses, except that the mice in model control group were orally administered with 0.25% CMC-Na. Blood samples were taken before administration and at 2, 4, 10, 24, 34, 48, 58, 72 and 96 h after administration, and the serum was separated to determine serum DPP-IV activity.

Method for determining the serum DPP-IV activity: to 5 µL serum sample was added 45 µL of 80 mM $MgCl_2$ buffer, mixed well, and pre-incubated at room temperature for 5 minutes; thereto were added 10 µL of 0.1 mM the reaction substrate Gly-Pro-7-AMC and 40 µL buffer, and kept away from light; after mixing well, fluorescence determination was performed (excitation wave 380 nm/emission wave 460 nm) every 3 minutes for 18 minutes with a total of 6 times; time-fluorescence curve was made based on the determination results minus the blank background, in which the slope was activity value; the serum DPP-IV activity at 0 h before administration was setted as 100%; and a specific activity at each time point after administration was calculated according to the following formula: specific activity (%)=activity after administration/activity before administration×100%.

Experimental results: after ob/ob mice were orally administered once with the compound of Example 4 at various doses, the serum DPP-IV activity was significantly inhibited in dose- and time-dependent manner. The inhibitory rate of serum DPP-IV activity in mice was higher than 70% over 10 hours after the administration of 1 mg/kg compound of Example 4. The inhibitory rate of serum DPP-IV activity in mice was higher than 70% over 24 hours after the administration of 3 mg/kg compound of Example 4. The inhibitory rate of serum DPP-IV activity in mice was higher than 70% over 34 hours after the administration of 10 mg/kg compound of Example 4. The inhibitory rate of serum DPP-IV activity in mice was higher than 70% over 72 hours after the administration of 30 mg/kg compound of Example 4. The inhibitory rate of serum DPP-IV activity in mice in the 30 mg/kg Omarigliptin (as the positive control) group was higher than 70% over 34 hours after administration.

| Group | Dose (mg/kg) | Specific activity of DPP-IV at various time points after administration (%) | | | | | | | | | |
|---|---|---|---|---|---|---|---|---|---|---|---|
| | | 0 h | 2 h | 4 h | 10 h | 24 h | 34 h | 48 h | 58 h | 72 h | 96 h |
| Model Control | — | 100 | 92.6 | 80.7 | 71.3 | 82.7 | 86.2 | 85.6 | 83.4 | 96.2 | 100.4 |
| Omarigliptin | 30 | 100 | 8.4 | 7.4 | 9.1 | 15.6 | 20.2 | 45.5 | 41.2 | 58.4 | 68.0 |
| Compound of Example 4 | 1 | 100 | 2.5 | 3.4 | 4.0 | 32.6 | 44.0 | 85.3 | 77.3 | 95.9 | 104.3 |
| | 3 | 100 | 2.4 | 2.3 | 3.0 | 24.9 | 32.2 | 65.4 | 58.7 | 80.7 | 87.0 |
| | 10 | 100 | 2.2 | 3.2 | 3.1 | 9.0 | 12.8 | 41.3 | 39.5 | 64.8 | 75.3 |
| | 30 | 100 | 2.3 | 3.9 | 4.4 | 7.3 | 6.9 | 19.2 | 18.6 | 29.3 | 40.4 |

What is claimed is:

1. A compound having the following formula (IV):

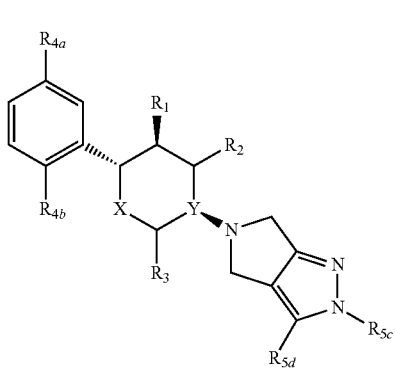

IV wherein,
X is O;
Y is selected from the group consisting of N and CH;
$R_1$ is selected from the group consisting of —$NH_2$ and —OH;
$R_2$ and $R_3$ are both H;
$R_{4a}$ and $R_{4b}$ are each independently selected from the group consisting of F, Cl, Br, —$NH_2$ and —OH;
$R_{5c}$ and $R_{5d}$ together with the atoms of pyrazole ring to which they are attached form a 5, 6 or 7-membered non-aromatic ring, and
a pharmaceutically acceptable salt thereof.

2. A compound having the following formula (V):

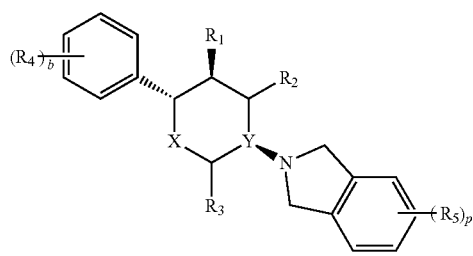

V wherein the substitution position of $R_5$ is positions of $R_{5a}$ and $R_{5b}$ shown in the structure represented by formula VII or formula VIII:

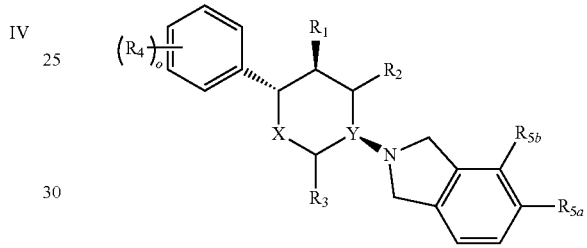

wherein,
X is O;
Y is selected from the group consisting of N and CH;
$R_1$ is selected from the group consisting of —$NH_2$ and —OH;
$R_2$ and $R_3$ are both H;
each $R_4$ is independently selected from the group consisting of F, Cl, Br, $NH_2$, and OH;
$R_{5a}$ is selected from the group consisting of —$NHR_7$ and —$SO_2R_8$;
$R_{5b}$ is selected from the group consisting of F Cl Br and I;
$R_7$ is —$SO_2R_8$,
each $R_8$ is independently selected from the group consisting of —OH, —$NH_2$, $C_{1-6}$ alkyl and $C_{3-6}$ cycloalkyl; and
o is independently 1, 2 or 3, p is 1 or 2, and
a pharmaceutically acceptable salt thereof.

3. The compound of claim 2, wherein each $R_8$ is independently selected from the group consisting of —OH, —$NH_2$, methyl, ethyl, propyl, butyl, $C_3$ cycloalkyl, $C_4$ cycloalkyl and $C_5$ cycloalkyl.

4. The compound of claim 2, wherein o is 2.

5. The compound of claim 2, wherein a substitution position of $R_4$ is positions of $R_{4a}$ and $R_{4b}$ shown in the structure represented by formula VI:

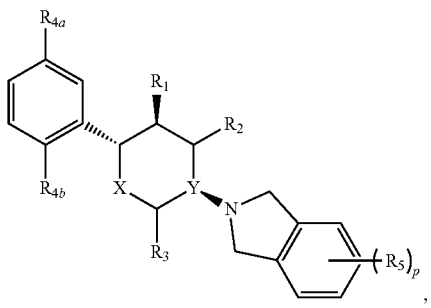

wherein $R_{4a}$ and $R_{4b}$ are each independently selected from the group consisting of F, Cl, Br, I, —$NH_2$ and OH; $R_5$ is defined the same as $R_{5a}$ when p is 1; $R_5$s are defined the same as $R_{5a}$ and $R_{5b}$, respectively, when p is 2; and the remaining groups are defined the same as in claim 2.

6. The compound of claim 2 selected from the group consisting of the following:

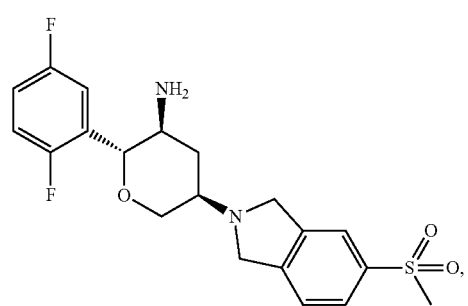

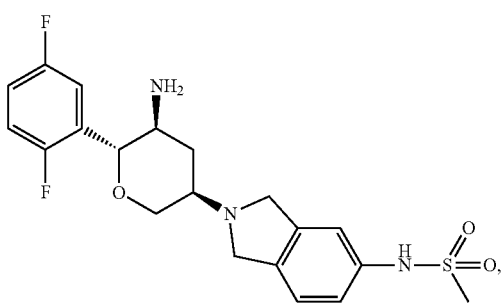

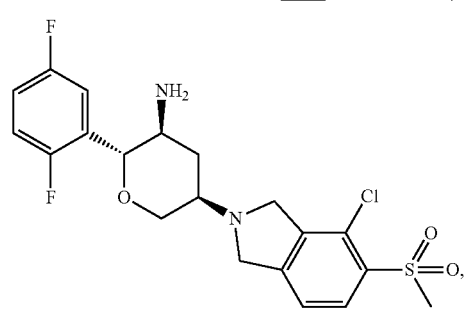

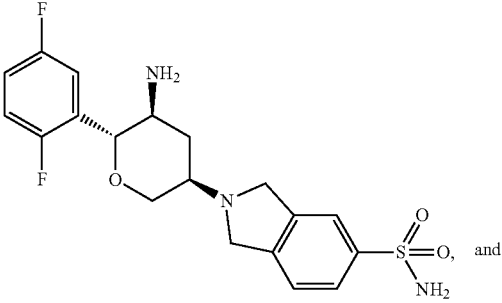

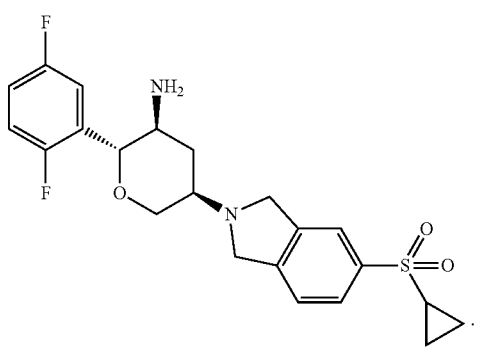

7. A pharmaceutical composition, comprising the compound of claim 2, or a pharmaceutically acceptable salt thereof, and a pharmaceutical acceptable carrier.

8. A method for the treatment of diseases and disorders benefitting from DPP-IV inhibition, comprising administering to a subject in need thereof the compound of claim 2, or a pharmaceutically acceptable salt thereof, wherein the diseases and disorders benefitting from DPP-IV inhibition are type II diabetes.

9. A method for the treatment of diseases and disorders benefitting from DPP-IV inhibition, comprising administering to a subject in need thereof the pharmaceutical composition of claim 7, wherein the diseases and disorders benefitting from DPP-IV inhibition are type II diabetes.

10. The compound of claim 1, wherein the 5, 6 or 7-membered non-aromatic ring contains 1, 2 or 3 heteroatoms independently selected from the group consisting of N, O and S.

11. The compound of claim 10, wherein the 5, 6 or 7-membered non-aromatic ring contains an —$SO_2$— group.

12. The compound of claim 1, which has the following structure:

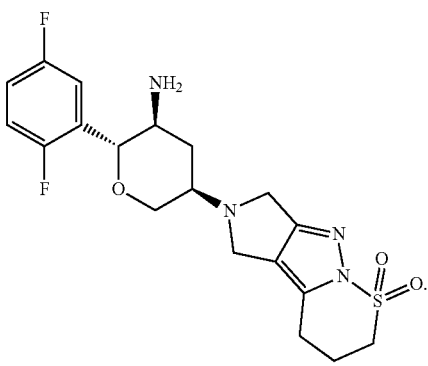 [SMILES: N[C@H]1C[C@@H](N2Cc3nn4c(c3C2)CCCS4(=O)=O)CO[C@@H]1c1cc(F)ccc1F]

13. A pharmaceutical composition, comprising the compound of claim 1, or a pharmaceutically acceptable salt and a pharmaceutical acceptable carrier.

14. A method for the treatment of diseases and disorders benefitting from DPP-IV inhibition, comprising administering to a subject in need thereof the compound of claim 1, or a pharmaceutically acceptable salt thereof, wherein the diseases and disorders benefitting from DPP-IV inhibition are type II diabetes.

15. A method for the treatment of diseases and disorders benefitting from DPP-IV inhibition, comprising administering to a subject in need thereof the pharmaceutical composition of claim 13, wherein the diseases and disorders benefitting from DPP-IV inhibition are type II diabetes.

16. A compound having the following structure:

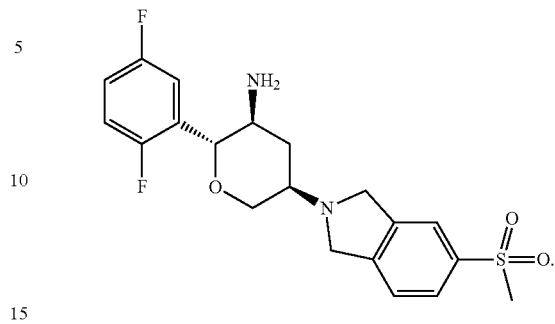

17. A pharmaceutical composition, comprising the compound of claim 16, or a pharmaceutically acceptable salt and a pharmaceutical acceptable carrier.

18. A method for the treatment of diseases and disorders benefitting from DPP-IV inhibition, comprising administering to a subject in need thereof the compound of claim 16, or a pharmaceutically acceptable salt thereof, wherein the diseases and disorders benefitting from DPP-IV inhibition are type II diabetes.

19. A method for the treatment of diseases and disorders benefitting from DPP-IV inhibition, comprising administering to a subject in need thereof the pharmaceutical composition of claim 17, wherein the diseases and disorders benefitting from DPP-IV inhibition are type II diabetes.

* * * * *